(12) United States Patent
Holupka et al.

(10) Patent No.: US 7,171,255 B2
(45) Date of Patent: *Jan. 30, 2007

(54) VIRTUAL REALITY 3D VISUALIZATION FOR SURGICAL PROCEDURES

(75) Inventors: Edward J. Holupka, Medway, MA (US); Everette C. Burdette, Champaign, IL (US); Irving D. Kaplan, Newton, MA (US)

(73) Assignee: Computerized Medical Systems, Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/897,326

(22) Filed: Jul. 2, 2001

(65) Prior Publication Data

US 2001/0041838 A1 Nov. 15, 2001

Related U.S. Application Data

(63) Continuation of application No. 08/977,362, filed on Nov. 24, 1997, now Pat. No. 6,256,529, which is a continuation-in-part of application No. 08/507,199, filed on Jul. 26, 1995, now Pat. No. 5,810,007.

(51) Int. Cl.
*A61B 5/05* (2006.01)

(52) U.S. Cl. .......................... 600/427; 600/439; 600/3; 600/7; 600/8

(58) Field of Classification Search ................ 600/439, 600/437, 431, 427, 407, 411, 1–3, 7, 424, 600/443, 8; 606/130

See application file for complete search history.

(56) References Cited

U.S. PATENT DOCUMENTS

| | | | |
|---|---|---|---|
| 4,125,858 A | 11/1978 | Hounsfield et al. | |
| 4,567,896 A | 2/1986 | Barnea et al. | |
| 4,586,512 A | 5/1986 | Do-huu et al. | |
| 4,751,643 A | 6/1988 | Lorensen et al. | |
| 4,764,971 A | 8/1988 | Sullivan | |
| 4,791,567 A | 12/1988 | Cline et al. | |
| 4,856,074 A | 8/1989 | Nagaoka | |

(Continued)

FOREIGN PATENT DOCUMENTS

DE 198 25 999 12/1999

(Continued)

OTHER PUBLICATIONS

Patent Cooperation Treaty; International Search Report; May 17, 2004.

(Continued)

*Primary Examiner*—Ruth S. Smith
(74) *Attorney, Agent, or Firm*—Thompson Coburn, LLP

(57) ABSTRACT

A method and apparatus for three-dimensional imaging and treatment of a patient's body. The method and apparatus utilize a system for developing a therapy plan for treatment of an organ of the patient, a device for generating ultrasound image data from a treatment region and a device for providing a translucent volume image of a portion of a patient's body and a separate translucent image of the patient organ and a three dimensional viewing device to superimpose a translucent article image to enable viewing of the article image simultaneously with the patient organ and a portion of the patient's body.

45 Claims, 13 Drawing Sheets

U.S. PATENT DOCUMENTS

| | | | |
|---|---|---|---|
| 4,896,673 A | 1/1990 | Rose et al. | |
| 4,961,425 A | 10/1990 | Kennedy et al. | |
| 4,991,579 A | 2/1991 | Allen | |
| 4,994,013 A * | 2/1991 | Suthanthiran et al. | 600/8 |
| 5,072,384 A | 12/1991 | Doi et al. | |
| 5,133,020 A | 7/1992 | Giger et al. | |
| 5,166,876 A | 11/1992 | Cline et al. | |
| 5,170,790 A | 12/1992 | Lacoste et al. | |
| 5,178,148 A | 1/1993 | Lacoste et al. | |
| 5,185,809 A | 2/1993 | Kennedy et al. | |
| 5,187,658 A | 2/1993 | Cline et al. | |
| 5,204,625 A | 4/1993 | Cline et al. | |
| 5,222,499 A | 6/1993 | Allen et al. | |
| 5,227,969 A | 7/1993 | Waggener et al. | |
| 5,234,004 A | 8/1993 | Hascoet et al. | |
| 5,239,591 A | 8/1993 | Ranganath | |
| 5,242,373 A | 9/1993 | Scott et al. | |
| 5,260,871 A | 11/1993 | Goldberg | |
| 5,289,374 A | 2/1994 | Doi et al. | |
| 5,299,253 A | 3/1994 | Wessels | |
| 5,319,549 A | 6/1994 | Katsuragawa et al. | |
| 5,319,551 A | 6/1994 | Sekiguchi et al. | |
| 5,339,812 A | 8/1994 | Hardy et al. | |
| 5,371,810 A | 12/1994 | Vaidyanathan | |
| 5,389,101 A | 2/1995 | Heilbrun et al. | |
| 5,391,139 A * | 2/1995 | Edmundson | 600/7 |
| 5,391,199 A | 2/1995 | Ben-Haim | |
| 5,394,457 A | 2/1995 | Leibinger et al. | |
| 5,398,690 A * | 3/1995 | Batten et al. | 600/461 |
| 5,409,006 A | 4/1995 | Buchholtz et al. | |
| 5,410,617 A | 4/1995 | Kidd et al. | |
| 5,411,026 A | 5/1995 | Carol | |
| 5,412,563 A | 5/1995 | Cline et al. | |
| 5,433,199 A | 7/1995 | Cline et al. | |
| 5,447,154 A | 9/1995 | Cinquin et al. | |
| 5,452,367 A | 9/1995 | Bick et al. | |
| 5,457,754 A | 10/1995 | Han et al. | |
| 5,458,126 A | 10/1995 | Cline et al. | |
| 5,460,592 A | 10/1995 | Langton et al. | |
| 5,491,627 A | 2/1996 | Zhang et al. | |
| 5,494,039 A | 2/1996 | Onik et al. | |
| 5,517,602 A | 5/1996 | Natarajan | |
| 5,526,812 A * | 6/1996 | Dumoulin et al. | 600/407 |
| 5,531,223 A | 7/1996 | Hatanaka | |
| 5,531,227 A | 7/1996 | Schneider | |
| 5,537,485 A | 7/1996 | Nishikawa et al. | |
| 5,553,207 A | 9/1996 | Sekiguchi et al. | |
| 5,562,095 A * | 10/1996 | Downey et al. | 600/445 |
| 5,566,246 A | 10/1996 | Rao | |
| 5,570,430 A | 10/1996 | Sheehan et al. | |
| 5,574,799 A | 11/1996 | Bankman et al. | |
| 5,583,659 A | 12/1996 | Lee et al. | |
| 5,590,215 A | 12/1996 | Allen | |
| 5,603,318 A | 2/1997 | Heilbrun et al. | |
| 5,622,170 A | 4/1997 | Schulz | |
| 5,624,382 A | 4/1997 | Oppelt et al. | |
| 5,638,819 A | 6/1997 | Manwaring et al. | |
| 5,640,496 A | 6/1997 | Hardy et al. | |
| 5,660,185 A | 8/1997 | Shmulewitz et al. | |
| 5,662,111 A | 9/1997 | Cosman | |
| 5,669,382 A | 9/1997 | Curwen et al. | |
| 5,672,172 A * | 9/1997 | Zupkas | 606/20 |
| 5,682,886 A | 11/1997 | Delp et al. | |
| 5,715,836 A | 2/1998 | Kliegis et al. | |
| 5,727,538 A | 3/1998 | Ellis | |
| 5,734,739 A | 3/1998 | Sheehan et al. | |
| 5,740,225 A | 4/1998 | Nabatame | |
| 5,742,263 A | 4/1998 | Wang et al. | |
| 5,749,362 A | 5/1998 | Funda et al. | |
| 5,765,561 A | 6/1998 | Chen et al. | |
| 5,769,074 A | 6/1998 | Barnhill et al. | |
| 5,776,063 A | 7/1998 | Dittrich et al. | |
| 5,797,849 A | 8/1998 | Vesely et al. | |
| 5,810,007 A | 9/1998 | Holupka et al. | |
| 5,817,022 A | 10/1998 | Vesely | |
| 5,830,145 A | 11/1998 | Tenhoff | |
| 5,833,627 A | 11/1998 | Shmulewitz et al. | |
| 5,836,954 A | 11/1998 | Heilbrun et al. | |
| 5,851,183 A | 12/1998 | Bucholz | |
| 5,859,891 A | 1/1999 | Hibbard | |
| 5,860,909 A | 1/1999 | Mick et al. | |
| 5,868,673 A | 2/1999 | Vesely | |
| 5,868,757 A | 2/1999 | Koutrouvelis | |
| 5,871,448 A * | 2/1999 | Ellard | 600/459 |
| 5,906,574 A | 5/1999 | Kan | |
| 5,928,130 A | 7/1999 | Schmidt | |
| 5,931,786 A | 8/1999 | Whitmore, III et al. | |
| 5,938,583 A | 8/1999 | Grimm | |
| 5,951,571 A | 9/1999 | Audette | |
| 5,961,527 A | 10/1999 | Whitmore, III et al. | |
| 5,974,165 A | 10/1999 | Giger et al. | |
| 5,984,870 A | 11/1999 | Giger et al. | |
| 5,989,811 A | 11/1999 | Veltri et al. | |
| 6,004,267 A | 12/1999 | Tewari et al. | |
| 6,006,126 A | 12/1999 | Cosman | |
| 6,007,474 A | 12/1999 | Rydell | |
| 6,025,128 A | 2/2000 | Veltri et al. | |
| 6,027,446 A | 2/2000 | Pathak et al. | |
| 6,033,357 A | 3/2000 | Ciezki et al. | |
| 6,036,632 A | 3/2000 | Whitmore, III et al. | |
| 6,038,467 A | 3/2000 | De Bliek et al. | |
| 6,048,312 A | 4/2000 | Ishrak et al. | |
| 6,083,166 A | 7/2000 | Holdaway et al. | |
| 6,083,167 A | 7/2000 | Fox et al. | |
| 6,095,975 A * | 8/2000 | Silvern | 600/439 |
| 6,102,844 A | 8/2000 | Ravins et al. | |
| 6,102,867 A | 8/2000 | Dietz et al. | |
| 6,129,670 A | 10/2000 | Burdette et al. | |
| 6,140,065 A | 10/2000 | Carlson et al. | |
| 6,146,390 A | 11/2000 | Heilbrun et al. | |
| 6,165,181 A | 12/2000 | Heilbrun et al. | |
| 6,167,296 A * | 12/2000 | Shahidi | 600/427 |
| 6,179,768 B1 | 1/2001 | Loffler et al. | |
| 6,196,963 B1 | 3/2001 | Williams | |
| 6,196,964 B1 | 3/2001 | Loffler et al. | |
| 6,206,832 B1 | 3/2001 | Downey et al. | |
| 6,208,883 B1 | 3/2001 | Holupka et al. | |
| 6,210,315 B1 | 4/2001 | Andrews et al. | |
| 6,213,110 B1 | 4/2001 | Christopher et al. | |
| 6,213,932 B1 | 4/2001 | Schmidt | |
| 6,236,875 B1 | 5/2001 | Bucholz et al. | |
| 6,238,342 B1 | 5/2001 | Feleppa et al. | |
| 6,241,670 B1 | 6/2001 | Nambu | |
| 6,249,594 B1 | 6/2001 | Hibbard | |
| 6,256,529 B1 * | 7/2001 | Holupka et al. | 600/427 |
| 6,261,219 B1 | 7/2001 | Meloul et al. | |
| 6,266,453 B1 | 7/2001 | Hibbard et al. | |
| 6,270,472 B1 | 8/2001 | Antaki et al. | |
| 6,301,495 B1 | 10/2001 | Gueziec et al. | |
| 6,311,084 B1 * | 10/2001 | Cormack et al. | 600/411 |
| 6,325,758 B1 | 12/2001 | Carol et al. | |
| 6,354,989 B1 | 3/2002 | Nudeshima | |
| 6,358,195 B1 | 3/2002 | Green et al. | |
| 6,361,487 B1 | 3/2002 | Green et al. | |
| 6,366,796 B1 | 4/2002 | Yanof et al. | |
| 6,387,034 B1 | 5/2002 | Lee | |
| 6,387,035 B1 | 5/2002 | Jung, Jr. et al. | |
| 6,416,492 B1 | 7/2002 | Nielson | |
| 6,454,696 B1 | 9/2002 | Kindlein et al. | |
| 6,500,109 B2 | 12/2002 | Tokita et al. | |
| 6,512,942 B1 | 1/2003 | Burdette et al. | |
| 6,572,525 B1 | 6/2003 | Yoshizumi | |
| 2001/0029334 A1 | 10/2001 | Graumann et al. | |
| 2002/0077546 A1 | 6/2002 | Aldefeld et al. | |

| | | | |
|---|---|---|---|
| 2002/0087080 A1 | 7/2002 | Slayton et al. | |
| 2003/0074011 A1 | 4/2003 | Gilboa et al. | |

FOREIGN PATENT DOCUMENTS

| | | |
|---|---|---|
| EP | 0 424 912 | 5/1991 |
| EP | 0 455 439 A2 | 11/1991 |
| WO | WO 91/07726 | 5/1991 |
| WO | WO 96/10949 | 4/1996 |
| WO | WO 96/11624 | 4/1996 |
| WO | WO 96/42070 | 12/1996 |
| WO | WO 98/39736 | 9/1998 |
| WO | WO 00/14668 | 3/2000 |
| WO | WO 00/63658 | 10/2000 |
| WO | WO 01/06924 | 2/2001 |
| WO | WO 01/87164 | 11/2001 |
| WO | WO 01/95795 | 12/2001 |
| WO | WO 02/44749 | 6/2002 |

OTHER PUBLICATIONS

Patent Cooperation Treaty; Supplementary European Search Report; Nov. 15, 2001.
Adams and Bischof; "Seeded Region Growing"; *IEEE Transactions on Pattern Analysis and Machine Intelligence*; Jun. 1994; pp. 641-647; vol. 16, No. 6.
Anuta, P.E., Oct. 1970 IEEE Transactions on Geoscience Electronics, vol. GE-8, No. 4, "Spatial Registration of Multispectrical and Multitemporal Digital Imagery Using Fast Fourier Transform Techniques", pp. 353-368.
Ballard and Brown; *Computer Vision*; 1982; pp. 119-165; Chapters 4-5; Prentice-Hall, Inc., Englewood Cliffs, New Jersey.
Barnea and Silverman, Feb. 1972 IEEE Transactions on Computers, vol. C-21, No. 2, "A Class of Algorithms for Fast Digital Image Registration", pp. 179-186.
Besag; "On the Statistical Analysis of Dirty Pictures"; *Journal of the Royal Statistical Society*; 1986; pp. 259-279; vol. 48, No. 3.
Beveridge, Griffith, Kohler, Hanson and Riseman; "Segmenting Images Using Localized Histograms adn Region Merging"; *International Journal of Computer Vision*; 1989; pp. 311-347; vol. 2; Kluwer Academic Publishers, Boston.
Bezdek et al.; "Review of MR image segmentation techniques using pattern recognition"; Medical Physics; vol. 20(4); pp. 1033-1048; 1993.
Brown, L.G., Dec. 1992 ACM Computing Surveys vol. 24 No. 4, "A Survey of Image Registration Techniques", pp. 325-378.
Chakraborty et al.; Deformable boundary finding in medical images by integrating gradient and region information; IEEE Transactions on Medical Imaging; vol. 15; pp. 859-870; 1996.
Cline et al. "3D reconstruction of the brain from magnetic resonance images using a connectivity algorithm"; Magnetic Resonance Imaging; vol. 5; pp. 345-352; 1987.
Cline et al.; "Three-dimensional segmentation of MR images of the head using probability and connectivity"; Journal of Computer Assisted Tomography; vol. 14(6); pp. 1037-1045; 1990.
Cline et al.; "Vascular morphology by three-dimensional magnetic resonance imaging"; Magnetic Resonance Imaging; vol. 7; pp. 45-54; 1989.
Cohen; "On Active Contour Models and Balloons"; *CVGIP: Image Understanding*; Mar. 1991; pp. 211-218; vol. 53, No. 2; Academic Press, Inc.
Collignon, A., et al., Apr. 1995 Proc. of the Xvth Int'l. Conf. On Computer Vision, Virtual Reality, and Robotics in Medicine (CVRMed '95), vol. 905, "Automated Multi-Modality Image Registration Based On Information Theory", pp. 263-274.
Cover and Thomas; *Elements of Information Theory*; 1991; pp. 12-42, 279-332; Chapters 2, 12; John Wiley & Sons, Inc., New York.
Decarli et al.; "Method for quantification of brain, ventricular, and subarachnoid CSF volumes from MR images"; Journal of Computer Assisted Tomography; vol. 16(2); pp. 274-284; 1992.
Delagnes et al.; "Active contours approach to object tracing in image sequences with complex background"; Pattern Recognition Letters; vol. 16(2); pp. 171-178; 1995.

Devroye, Györfi and Lugosi; *A Probabilistic Theory Pattern Recognition*; 1996; pp. 9-20, 61-90; Chapters 2, 5; Springer-Verlag New York, Inc.
Diallo, B.; "Conception, realisation et exploitation d'une base de donnees en neuroimagerie cognitive"; Universite de Caen/Basse-Normandi; Mar. 1992; pp. 148-180; Caen, France.
Duda, Hart and Stork; *Pattern Classification*; 2001; pp. 20-83, 161-214; Second Edition, Chapters 2, 4; John Wiley & Sons, Inc., New York.
Duda, Hart and Stork; *Pattern Classification*; 2001; pp. 517-599; Second Edition, Chapter 10; John Wiley & Sons, Inc., New York.
Fletcher et al.; A multispectral analysis of brain tissues; Magnetic Resonance in Medicine; vol. 29; pp. 623-630; 1993.
Fukunaga; *Introduction to Statistical Pattern Recognition*; 1990; pp. 51-123; Second Edition, Chapter 3; Academic Press, Inc., San Diego, California.
Geman and Geman; "Stochastic Relaxation, Gibbs Distributions, and the Bayesian Restoration of Images"; *IEEE Transactions on Pattern Analysis and Machine Intelligence*; Nov. 1984, pp. 721-741; vol. PAMI-6, No. 6.
Giardina and Kuhl; "Accuracy of Curve Approximation by Harmonically Related Vectors with Elliptical Loci"; *Computer Graphics and Image Processing*; 1977; pp. 277-285; vol. 6; Academic Press, Inc.
Gomez-Lopera J F et al.: "An analysis of edge detection by using the Jensen-Shannon divergence" Journal of Mathematical Imaging and Vision, vol. 13, No. 1, Aug. 2000, pp. 35-56, XP008033153 Kluwer Academic Publishers, Netherlands ISSN: 0924-9907 the whole document.
Grimmett and Stirzaker; *Probability and Random Processses*; 1992; pp. 1-21; Second Edition, Chapter 1; Oxford University Press, Oxford.
Haralick and Shapiro; "Image Segmentation Techniques"; *Computer Vision, Graphics, and Image Processing*; 1985; pp. 100-132; vol. 29.
He, Hamza and Krim; "An Information Divergence Measure for ISAR Image Registration"; IEEE Workshop on Statistical Signal Processing; Aug. 2001; Singapore.
Hibbard; "Maximum *a posteriori* Segmentation for Medical Visualization"; IEEE Workshop on Biomedical Image Analysis (WBIA98), Santa Barbara, California; Jun. 1998; pp. 93-102.
Hibbard, et al., Jun. 26, 1987 Science vol. 236, "Three-Dimensional Representation and Analysis of Brain Energy Metabolism", pp. 1641-1646.
Höhne et al.: "Interactive 3D segmentation of MRI and CT volumes using morphological operations"; Journal of Computer Assisted Tomography; vol. 16(2); pp. 285-294; 1992.
Holupka et al.; "Ultrasound image fusion for external beam radiotherapy for prostate cancer"; Int. J. Radiation Oncology Biol. Phys.; vol. 35, No. 5; pp. 975-984; 1996; Elsevier Science Inc., USA.
Kass, Witkin and Terzopoulos; "Snakes: Active Contour Models"; *International Journal of Computer Vision*; 1988; pp. 321-331; vol. 1, No. 4; Kluwer Academic Publishers, Boston.
Kohn et al.; "Analysis of brain and cerebrospinal fluid volumes with MR imaging"; Radiology; vol. 178; pp. 115-112; 1991.
Kuhl and Giardina; "Elliptic Fourier Features of a Closed Contour"; Computer Graphics and Image Processing; 1982; pp. 236-258; vol. 18; Academic Press, Inc.
Kullback and Leibler; "On Information and Sufficiency"; *Annals of Mathematical Statistics*; 1951; pp. 79-86; vol. 22.
Kullback; *Information Theory and Statistics*; 1959; pp. 1-35; Chapters 1, 2; Dover Publications, Inc., Mineola, New York.
Lin; "Divergence Measures Based on the Shannon Entropy"; *IEEE Transactions on Information Theory*; Jan. 1991; pp. 145-151; vol. 37, No. 1.
Maes, F., et al., Jun. 1996 IEEE Proceedings of MMBIA, "Multi-Modality Image Registration by Maximization of Mutual Information", pp. 14-22.
Malladi, Sethian and Vemuri; "Shape Modeling with Front Propagation: A Level Set Approach"; *IEEE Transactions on Pattern Analysis and Machine Intelligence*; Feb. 1995; pp. 158-175; vol. 17, No. 2.

McInerney et al.; Deformable models in medical image analysis; Proceedings of Mathematical Methods Biomedical Image Analysis; pp. 171-180; 1996.

Miller et al.; Matematical textbook of deformable neuroanatomies; Proceedings of the National Academy of Sciences USA; vol. 90; pp. 11944-11948; 1993.

Neal et al.; "Technical Note: Evaluation of a region growing algorithm for segmenting pelvic computed tomography images during radiotherapy planning"; The British Journal of Radiology; vol. 67; pp. 392-395; 1994.

Nocedal and Wright; *Numerical Optimization*; 1999; pp. 10-63; Chapters 2, 3; Springer-Verlag New York, Inc.

Pal and Pal; "A Review on Image Segmentation Techniques"; *Pattern Recognition*; 1993; pp. 1277-1294; vol. 26, No. 9; Great Britain.

Pelizzari, C.A., et al., Jan./Feb. 1989 Journal of Computer Assisted Tomography, vol. 13, No. 1, "Accurate Three-Dimensional Registration of CT, PET, and/or MR Images of the Brain", pp. 20-26.

Pietrzyk, U. et al.; "An Interactive technique for three-dimensional image registration: validation for PET, SPECT, MRI and CT brain studies"; The Journal of Nuclear Medicine; vol. 35, No. 12; Dec. 1994; pp. 2011-2018.

Pietrzyk, U. et al.; "Three-dimensional alignment of functional and morphological tomograms"; Journal of Computer Assisted Tomography; Jan.-Feb. 1990; vol. 14, No. 1; pp. 51-59; USA.

Pratt, W.K., May 1974 IEEE Transactions on Aerospace and Electronic Systems, vol. AES-10, No. 3, "Correlation Techniques of Image Registration", pp. 353-358.

Press, Teukolsky, Vetterling and Flannery; *Numerical Recipes in C++, The Art of Scientific Computing*; 2002; pp. 398-429; Second Edition; Chapter 10; Cambridge University Press, Cambridge, UK.

Principe; Xu and Fisher; "Information-Theoretic Learning" in *Unsupervised Adaptive Filtering*; 1999; pp. 265-319; Wiley, New York.

Rényi; "On Measures of Entropy and Information"; *Proceedings of the Fourth Berkley Symposium on Mathematical Statistics and Probability*; Berkeley, California, Jun.-Jul. 1960; Published 1961; pp. 547-561; vol. I; University of California Press.

Rényi; "Some Fundamental Questions of Information Theory"; *Selected Papers of Alfred Rényi*; 1976; pp. 526-552; vol. 2; Akademia Kiado, Budapest.

Rosenman, J.G., et al., 1998 Int. J. Radiation Oncology Biol. Phys., vol. 40, No. 1, "Image Registration: An Essential Part of Radiation Therapy Treatment Planning", pp. 197-205.

Rosenfeld and Kak; Digital Picture Processing; 1982; pp. 56-190; Second Edition, vol. 2, Chapter 10; Academic Press, New York.

Shannon; "A Mathematical Theory of Communication"; *The Bell System Technical Journal*; Jul., Oct. 1948; pp. 379-423, 623-656; vol. 27.

Staib and Duncan; "Boundary Finding with Parametrically Deformable Models"; *IEEE Transactions on Pattern Analysis and Machine Intelligence*; Nov. 1992; pp. 1061-1075; vol. 14, No. 11.

Studholme, C., et al., 1996 Medical Image Analysis, vol. 1, No. 2, "Automated 3-D Registration of MR and CT Images of the Head", pp. 163-175.

Tang and Ma; "General Scheme of Region Competition Based on Scale Space"; *IEEE Transactions on Pattern Analysis and Machine Intelligence*; Dec. 2001; pp. 1366-1378; vol. 23, No. 12.

Toennies, K. D. et al.; "Registration of 3D objects and surfaces"; IEEE Computer Graphics and Applications; vol. 10, No. 3; May 1, 1990; pp. 52-62; New York.

Unal G et al.: "Active polygons for object tracking" proceedings First International Symposium on 30 Data Processing Visualization and Transmission, Padova, Italy, Jun. 19-21, 2002, pp. 696-699, XP002290194 2002, Los Alamitos, CA, USA, IEEE Comput. Sox, USA ISBN: 0-7695-1521-5 sections 2, 3.

Vaidyanathan et al.; "Comparison of supervised MRI segmentation methods for tumor volume determination during therapy"; Magnetic Resonance Imaging: vol. 13(5): pp. 719-728; 1995.

Van Den Elsen, P.A., et al., Mar. 1993 IEEE Engineering in Medicine and Biology, "Medical Image Matching—A Review with Classification", pp. 26-39.

Van Herk, M., et al., Jul. 1994 Medical Physics, vol. 21, No. 7, "Automatic Three-Dimensional Correlation of CT-CT, CT-MRI, and CT-SPECT Using Chamfer Matching", pp. 1163-1178.

Van Trees; *Detection, Estimation, and Modulation Theory, Part I Detection, Estimation, and Linear Modulation Theory*; 1968; pp. 19-165; Chapter 2; John Wiley & Sons, Inc., New York.

Viola, P., et al. Jun. 1995 Proc of the Vth Int'l Conf. On Computer Vision, "Alignment by Maximization of Mutual Information", pp. 16-23.

Wells et al.; "Adaptive segmentation of MRI data"; IEEE Transactions on Medical Imaging; vol. 15, No. 4; pp. 429-442; 1996.

Witten and Frank; *Data Mining, Practical Machine Learning Tools and Techniques with Java Implementations*; 2000; pp. 157-227; Chapter 6; Morgan Kaufmann Publishers, San Francisco, California.

Yin et al.; "Comparison of bilateral-subtraction and single-image processing techniques in the computerized detection of mammographic masses"; Investigative Radiology; vol. 28(6); pp. 473-481; 1993.

\* cited by examiner

VIRTUAL REALITY 3D VISUALIZATION FOR SURGICAL PROCEDURES

This is a continuation of an Ser. No. 08/977,362 filed Nov. 24, 1997 (now U.S. Pat. No. 6,256,529) which is a continuation-in-part of Ser. No. 08/507,199 (now U.S. Pat. No. 5,810,007) filed Jul. 26, 1995.

The present invention is directed in general to an improved method and apparatus for carrying out minimally invasive treatments of the human body by virtual reality visualization of the treatment area. More particularly the invention is concerned with use of a three-dimensional ("3D") imaging probe apparatus and method for providing a real time, 3D, ultrasound, translucent rendering of a human anatomy undergoing treatment along with real time translucent rendering of treatment devices interacting with the organ. Such a methodology would be particularly useful as a system for guidance of minimally invasive surgical instruments within tissues to be treated as well as for deposition of radioactive seeds, or placement of other radioactive sources, and for radiotherapy of cancerous tissues in a human organ, such as the male prostate.

New minimally invasive surgical procedures are most often optically guided, but such optical guidance methods do not permit visualization and guidance of instruments or probes within (inside) the target tissue or organ. Incorporation of real-time 3D visualization inside diseased tissues would provide accurate guidance of therapy. Open-magnet MRI is used to visualize some procedures such as thermal therapy and brain biopsies. However, the method is expensive, not truly real-time, and is limited in application.

Numerous conventional treatment methods involve attempts to provide a targeted dosage of radiation or chemicals to the organ, and such treatments are often based on general anatomical assumptions of size and location. These methods suffer from inaccuracy of localizing the target for any one particular individual and potential real time changes of relative orientation and position of target tissue, normal tissue, and radiation therapy devices.

It is instructive in explaining the invention to consider one specific type of exemplary condition, adenocarcinoma of the male prostate which is the most commonly diagnosed cancer in the male population of the United States. At present, 254,000 new cases of prostate cancer were diagnosed in 1995 and 317,000 in 1996. In the 1960s, a method of implanting radioactive gold or iodine seeds was developed. With this approach, the radioactive material is permanently placed into the prostate via a retropubic approach during laparotomy when diagnostic lymphadenectomy was also being performed. A high dose of radiation is delivered to the prostate as the radioactive seeds decay. In several reports, the five year disease free survival ("local control") obtained by this method was compared to similarly staged patients treated with an external radiation beam. In view of this, gold was replaced by $I^{125}$ implantation for safety of personnel doing implantation. Except for early stage prostate cancer (T2a tumors), inferior rates of local control are reported with "free hand" 125-Iodine implantation. There was significant dose inhomogeneity due to the nonuniformity of seed placement, leading to underdosing of portions of the prostate gland and significant complications due to overdosing of adjacent healthy tissue structures. The poor results for local control and normal tissue complication were attributed to the doctor's inability to visualize and hence control where the radioactive seeds were actually being deposited inside the patient.

Recently, transrectal ultrasonography ("TRUS") has been used to visualize 125-Iodine seed placement during transperineal implantation. The early reported rates of serious late complications is higher than external beam therapy. Even with this technique, significant imprecisions in seed placement are observed. Due to the proximity of the prostate to the rectum and bladder, incorrect seed placement may lead to serious overdosing of these structures and late complications.

The recent transrectal ultrasound guided transperineal implant technique has been developed which is in use. That procedure is described in three steps: (1) the initial volumetric assessment of the prostate gland performed using ultrasound, (2) development of a radiation therapy "preplan," and (3) performing the actual intraoperative implant. The purpose of the initial volumetric assessment prior to the pre-plan or implantation is to obtain a quantitative understanding of the size of the prostate, which is then used to determine the total activity and distribution of radioactivity which is to be implanted into the prostate. To perform the assessment, an ultrasound probe is physically attached to a template. The template is a plastic rectangle which contains an array of holes separated at predefined intervals, usually 5 mm. The template system serves two purposes: (1) to fix the ultrasound probe, and hence the imaging plane to the reference frame of the catheter and seed positions, and (2) to guide the catheters into the prostate volume. More specifically, the template system serves as a reference frame for spatial quantities which are required for the description of the implant procedure. Using transrectal ultrasound, a number of serial ultrasound images are obtained at 5-mm intervals, and the prostate is outlined on each image. The images are taken so that the entire prostate gland is covered. This results in a stack of two-dimensional ("2D") outlines, or contours, which, taken together, outline the entire 3D prostate volume. From this volume, the quantitative volume of the prostate is calculated.

Once the 3D contour data has been obtained for the prostate volume, a radiation therapy plan which describes the positions of the radioactive seeds within the prostate is developed. This plan attempts to optimize the dose to the prostate, minimize the dose to surrounding healthy tissue, and minimize dose inhomogeneity. The positions of the radioactive seeds are constrained to fall within the catheter tracks, since the seeds are placed within the prostate transperineally via these catheters. The result of the pre-plan describes the positions and strengths of the radioactive seeds within the catheter which optimizes the dose to the prostate.

Intraoperatively, the TRUS probe is inserted, and the template is mounted against the perineum. As previously described, the template is a plastic rectangle which contains an array of holes separated at fixed intervals. These holes act as guides for the catheters. The TRUS probe is inserted into the rectum and placed so that the image corresponds to the prostate base (the maximum depth). Two or three catheters are inserted into the tissue surrounding the prostate or in the periphery of the prostate to immobilize the gland. These catheters contain no radioactive seeds. This image serves as a spatial reference for all further images and seed positions within the prostate. Subsequently, catheters are inserted into the gland based on the pre-plan through the template. The ultrasound probe is positioned each time so that the catheter, and hence seeds, which are inserted into the prostate are visible on the ultrasound image. If the placement of the catheter within the prostate is not according to the pre-plan, the catheter is then withdrawn and reinserted until the catheter is correctly placed. This is a time-consuming process; and it is very difficult to achieve optimal placement. Invariably, the catheters deflect angularly as they are inserted, and their positions are difficult to determine by 2D ultrasound. This is due to the fact that the visualization process is a 2D process while the actual implant procedure is 3D. Once all the seeds are in place, another series of 2D images are obtained to quantify the final, resultant dose distribution delivered to the patient. In some instances, a pair of orthogonal fluoroscopic images are also obtained to determine the final seed placements. This procedure is usually performed a few weeks post implant.

These above described prior art systems suffer from inherent inaccuracy, the inability to correct the positioning of the radioactive seeds without repeated withdrawal and reinsertion of seeds into the prostate and are not real time manipulations of the therapeutic medium. Further, the overall positioning of the template and patient may be different during treatment compared to the assessment phase. Consequently, the catheter position and seed position may be at an undesired position relative to the presumed assessment phase location.

It is therefore an object of the invention to provide an improved system and method for invasive treatment of the human body.

It is another object of the invention to provide a novel system and method for real time and/or near real time, 3D visualization of a human organ undergoing invasive treatment.

It is also an object of the present invention to provide a more precise and accurate implant placement for radiation therapy, thermal therapy, and surgical ablation.

It is also an object of the invention to provide an improved system and method for generating a 3D image data set of a human organ for a treatment protocol using a real-time ultrasound imaging system with spatial landmarks to relate the image data set to present time, invasive treatment devices.

It is a further object of the invention to provide a novel system and method for mapping the 3D images of a human organ, such as the male prostate, and using these images as a translucent colored volume enabling projection of real-time 3D virtual images to a physician performing invasive treatment manifested by virtual images of the treatment devices within the field of the virtual images of the organ.

It is an additional object of the invention to provide an improved method and system for 3D virtual imaging of the male prostate gland and overlaid virtual imaging of devices being inserted into the prostate for deposition of radioactive seeds for cancer therapy.

These and other objects and advantages of the invention will be readily apparent from the following description of the preferred embodiments thereof, taken in conjunction with the accompanying drawings described below.

BRIEF DESCRIPTION OF THE DRAWINGS

3B illustrates an anatomical prostate phantom used for testing and planning.

DETAILED DESCRIPTION OF PREFERRED EMBODIMENTS

Figure 1:
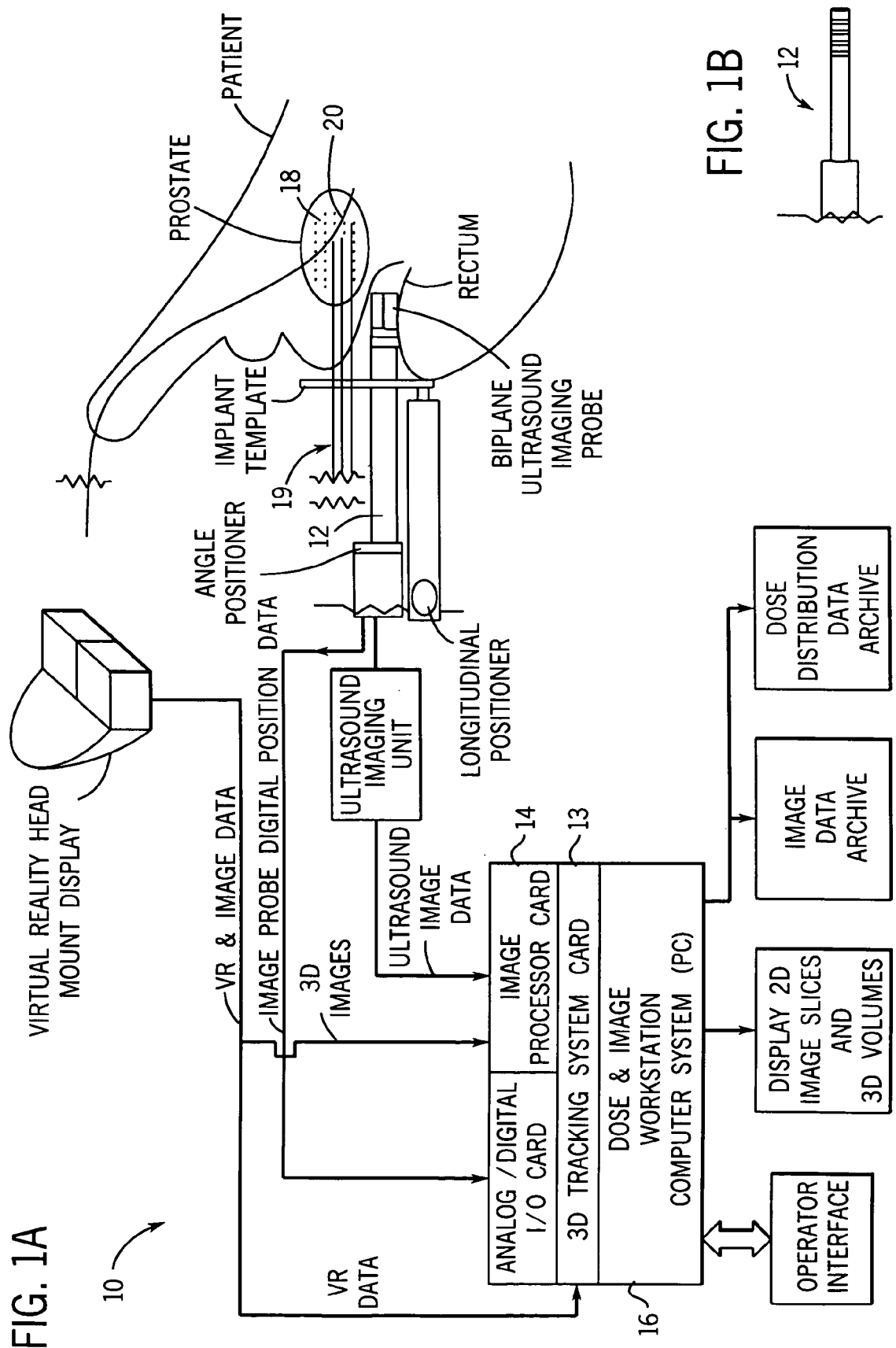
FIG. 1A illustrates a block diagram of an embodiment of the invention.
FIG. 1B shows an alternate embodiment for a three-dimensional probe.

A system 10 constructed in accordance with an example of the invention is illustrated generally in FIG. 1. A three-dimensional (3D) probe 12 accumulates image data from a treatment region or organ of a patient, image data is processed using a 3D imaging card 14. The probe 12 preferably is an ultrasound device but can be any other rapid imaging technology, such as rapid CT or MR. A conventional personal computer 16 having a monitor can be used to operate on the image data from the imaging card 14 using conventional software and hardware tools to be described in more detail hereinafter. Radioactive seeds 18 are provided for insertion using any one of a variety of conventional means for inserting devices or articles into the human body, such as insertion devices 19, which may be either needles or stiff catheters. The 3D ultrasound probe 12, therefore, provides an image signal to the computer 16 and a virtual realty interface card 13 coupled to the imaging card 14 which enables a user to visualize a translucent image of the patient organ and real time interaction of any one of a variety of treatment devices, such as the implant needles 19 or a Foley catheter 20, and one of the seeds 18 within the organ. Computer software can be utilized in a conventional manner to visualize the 3D imaging data in various formats. The formats include orthogonal two dimensional (2D) images, oblique 2D images, and translucent 3D rendering. All of these reconstructions can be directly displayed on the computer monitor; and 3D translucent, stereoscopic, rendering is also available in the VR (Virtual Realty) mode.

The preferred ultrasound probe 12 is a conventional Kretz ultrasound imaging system manufactured by Kretz Corporation, now available as Medison Combison 530 through Medison America Corporation, Pleasantown, Calif. This system and other such conventional systems are readily available and can provide real time ultrasound image data. The Medison Combison ultrasound system incorporates an endorectal probe which acquires multiple image planes in real time and the software of the present invention reconstructs the translucent 3D volume. Alternate systems include bi-plane 2D imaging systems with the probe mounted in a stepper motor driven holder for rapid automatic acauisition of multiple image planes. There is nothing that is application specific about the imaging system, thus any commercially available system will suffice.

Figure 2:
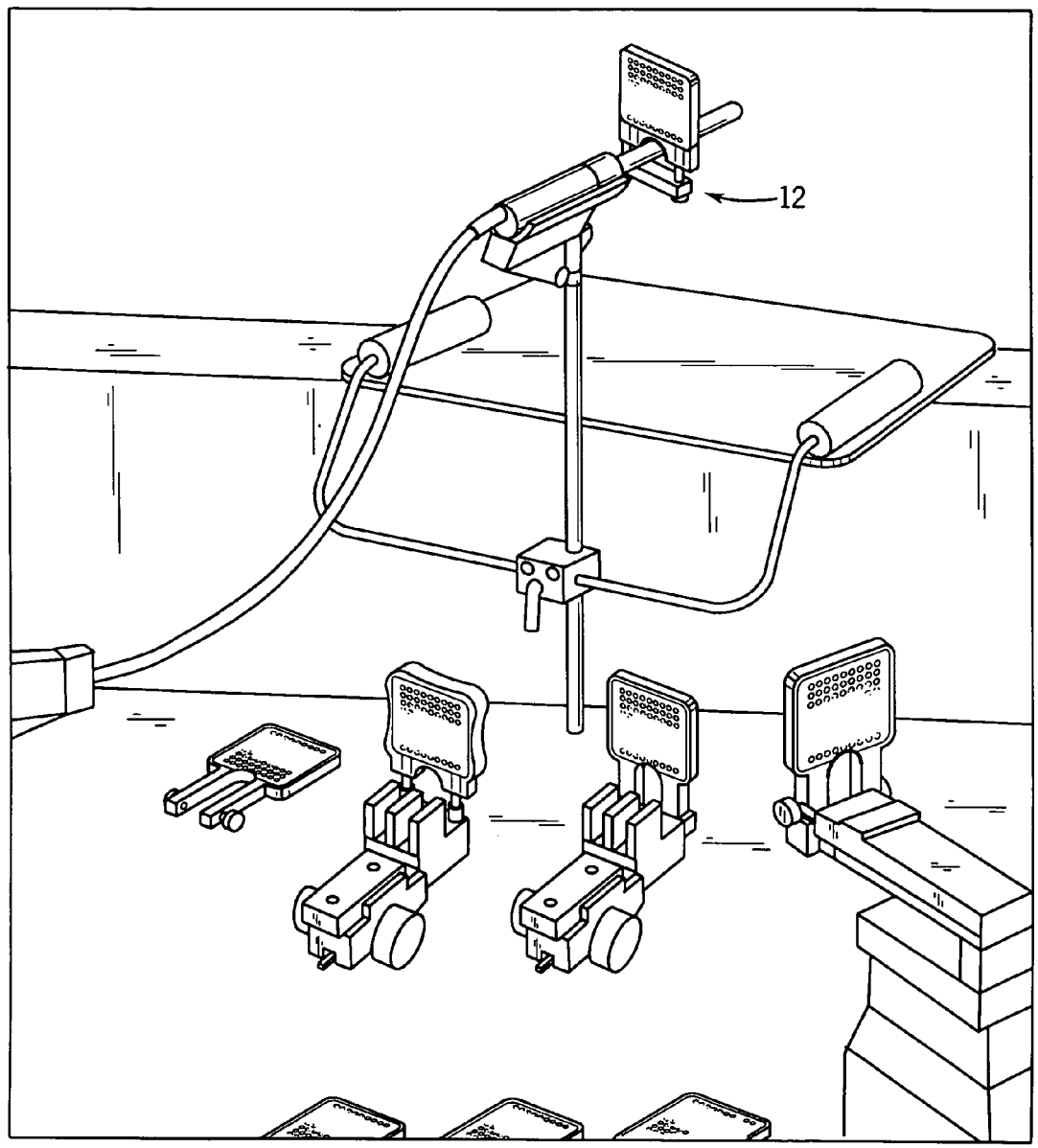
FIG. 2 illustrates an ultrasound guided implant system.

For collecting ultrasound image data, the diagnostic transrectal ultrasound probe 12 (see FIG. 2) is inserted into the patient's rectum to obtain real time volumetric images of the prostate for use during the implant procedure. The diagnostic probe 12 is preferably a phased array probe designed so that the array of transducers can rotate about the axis of the array sweeping out a 3D imaging volume. As the probe 12 rotates, images are captured and digitized by use of the imaging card 14 (see FIG. 1), so as to create a fixed number of images slices per rotation. An alternative method utilizes a transverse oriented phased array form of the endorectal probe 12 which is moved longitudinally in an automated rapid sequence so as to create a series of transverse image slices automatically. Another embodiment of the probe 12 can incorporate multiple transverse phased arrays (shown in phantom in FIG. 1B) arranged parallel to each other orthogonal to the axis of an endorectal probe to produce multiple simultaneous image slices (see, for example, FIGS. 5A and 5B). The 3D image data will be represented as a three dimensional image raster.

Figure 3A:
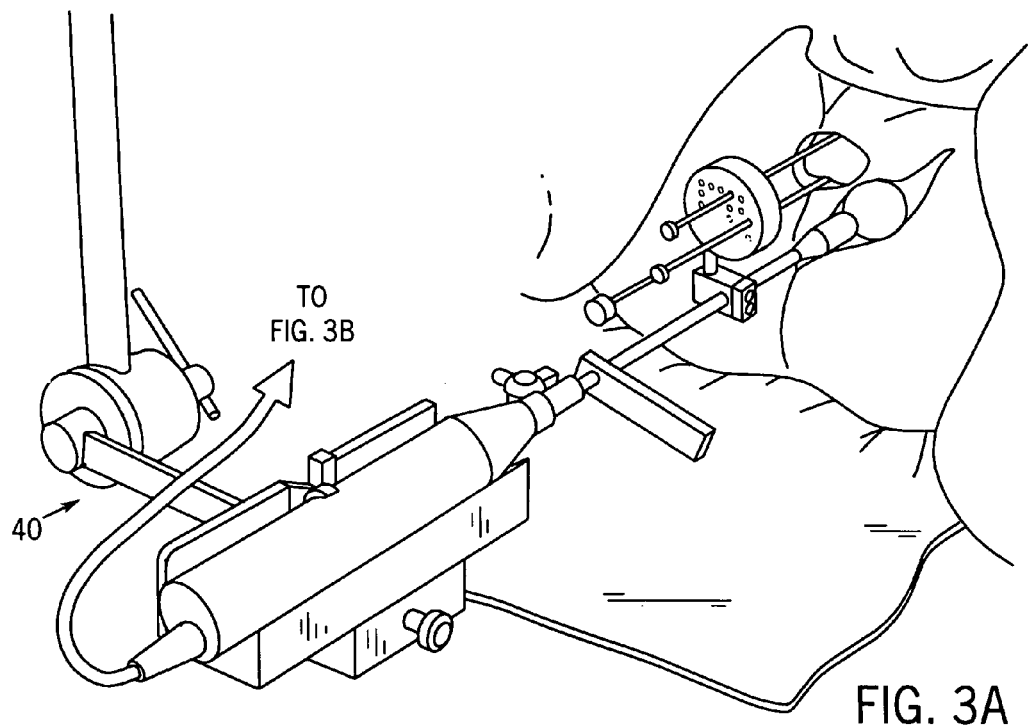
FIG. 3A illustrates patient setup for a radioactive implant procedure; FIG.
Figure 3B:
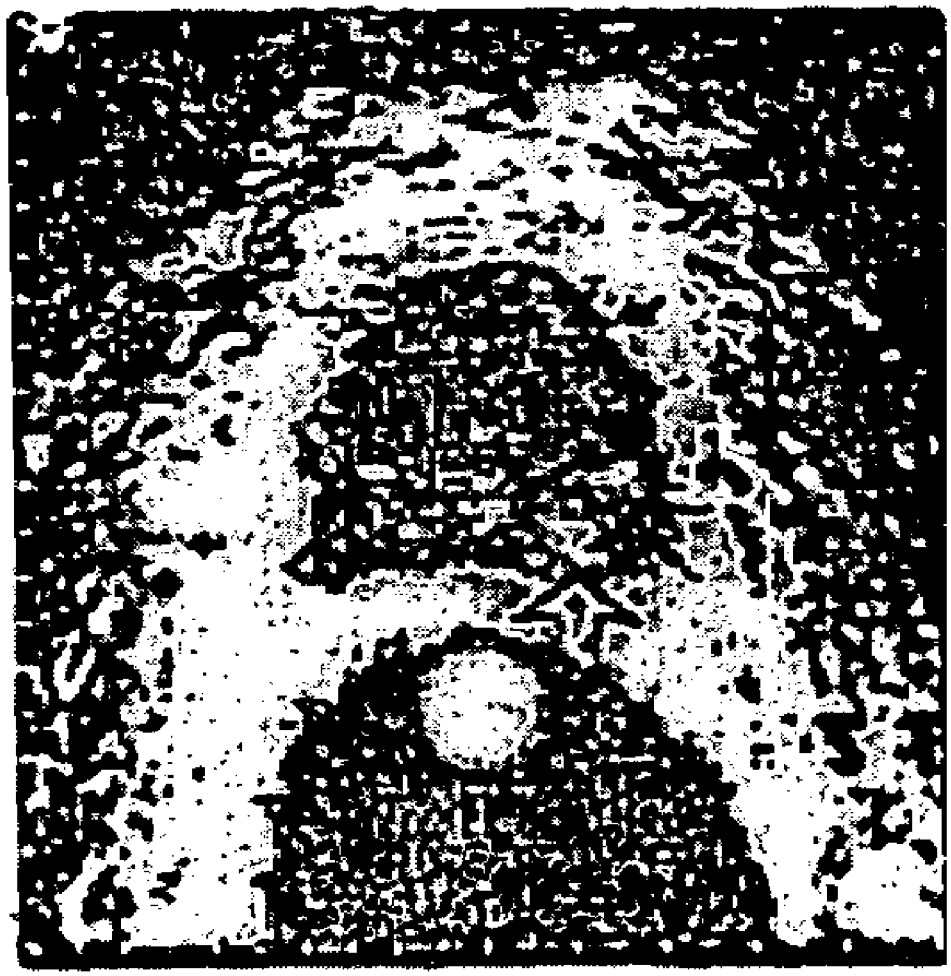
FIG. 3C illustrates in detail a probe holder/stepper assembly shown partly in FIG. 3A.
Figure 3C:
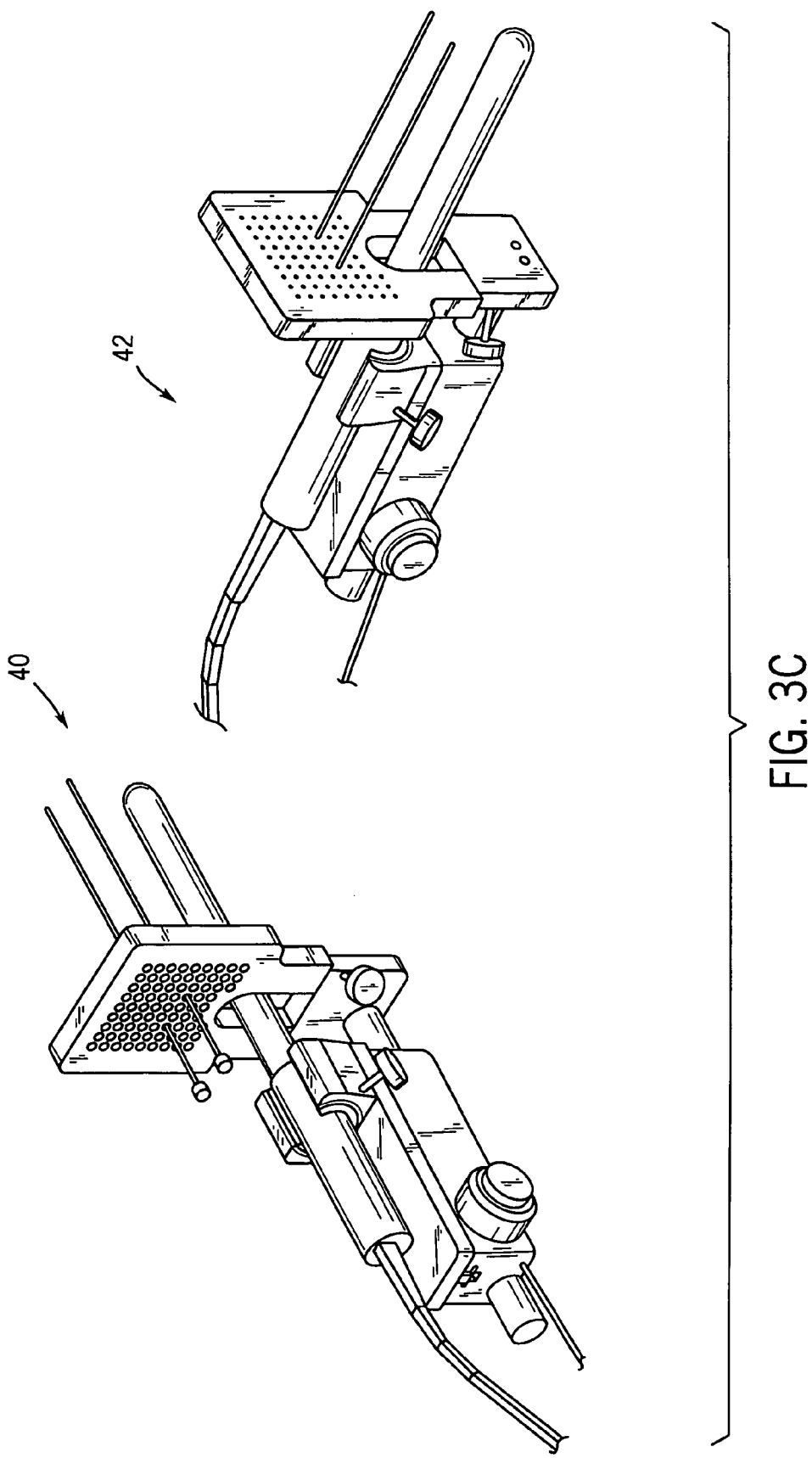
Figure 4A:
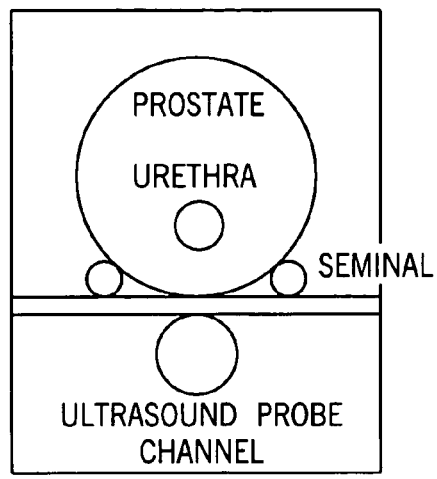
FIG. 4A illustrates a front schematic view of a brachytherapy phantom.
Figure 4B:
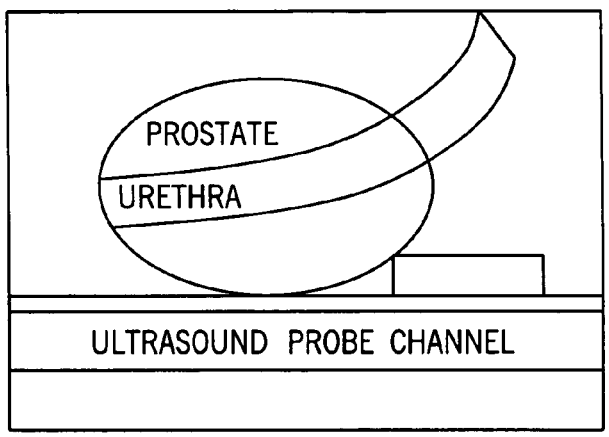
FIG. 4B a side schematic view of the brachytherapy phantom.

The ultrasound probe 12 can be mounted into a probe holder 30 (see FIGS. 3A and 3C) with FIG. 3B illustrating one example of an ultrasound image from an anatomical prostate phantom employed to carry out testing and planning. The probe holder 30 includes a digital encoder 42 for providing information regarding the position of all of the desired ultrasound image planes in the prostate relative to each other. The image plane location will be automatically sent to the system computer and "tagged" to the acquired ultrasound image for that position. Thus, it will be possible to reproduce the longitudinal and lateral positions of the implant catheters for the ultrasound therapy applicators and for the temperature probes.

There are several possible image processing cards which could be utilized; however, using current modalities each of the processing cards is configured specifically for 3D. The 3D image raster is buffered; and thus, for example, if the 2D images are 512×512 and there are sixteen image planes in the probe 12, and each pixel is a byte (256 gray scales), at least a 512×512×16 byte=4.2 Mbyte image buffer in the card 14 is needed. Several commercial cards (for example, made by Coreco, Matrox and Integral Technologies) can be equipped with this amount of video RAM (VRAM), but the way the card's hardware interacts with the computer's video and software drivers does not utilize this data in 3D. Current available methodologies enable augmenting the software and some hardware of these cards so that they can act as a 3D card. The processing and memory architecture preferably is designed to allow for simultaneous image acquisition and processing. The digitizing card should also preferably have standard imaging tools, such as real time window and leveling, zoom and pan of the ultrasound images. Some existing cards (e.g., Matrox; Coreco) do provide standard imaging tools.

The 3D image data arising from the ultrasound probe 12 is preferably buffered on the imaging card 14. The 3D image is preferably represented as a series of 2D images. This is referred to as the image stack or 3D image raster. The 3D image raster is represented in memory as a linear array of bytes of length N×M×P where N is the width of the 2D image in pixels, M is the height a 2D image in pixels, and P is the number of 2D images in the image stack.

In a preferred embodiment the user can include defined formats. Entire 3D image stacks at specific times during the intraoperative session can be stored in the DICOM standard. The user will have the ability to select a 3D image volume for archiving as part of the system software. These image stacks can then be reviewed in any of the various visualization modes (standard orthogonal 2D views, oblique 2D views, or 3D translucent views) as described above. In addition, the user will have the ability to store any of the 2D views available at any time during the intraoperative session.

The computational platform can, for example, be any form of computing means, such as the personal computer 16, which incorporates a PCI bus architecture. Currently, PCI bus is preferable over the ISA or EISA bus because the PCI bus is much faster. However, a generic system which will be suitable for this applicable will be described. A 200 Mhz (or greater speed) Pentium/Pentium-Pro computer supplied with 128 Mbytes of RAM and a 6.0 Gbyte hard disk should be sufficient RAM and disk memory to run the software in a real-time fashion and to archive all patient data. There should be sufficient RAM to facilitate host image processing in parallel with onboard image processing for quality assurance checks. A high resolution monitor capable of displaying at least 1280×1024×64 bit resolutions is preferably used.

Based on currently available technology, the ultrasound images obtained from the ultrasound imaging system of the ultrasound probe 12 can be of good diagnostic quality. When transforming this input image data into a 3D representation, whether in the 3D perspective mode or the real time VR mode, the resultant volumes can, however, be noisy and hinder diagnostic and spatial accuracy. In order to improve the image quality, a number of conventional hardware and software filters can be used which will filter the incoming image data stored on the imaging card 14. Routines such as image pixel averaging, smoothing, and interpolation can improve the 3D rendering of the imaging volume. These sets of filters or routines are to be distinguished from the set of standard imaging tools running on the host CPU which are available within a conventional imaging software package.

Figure 6:
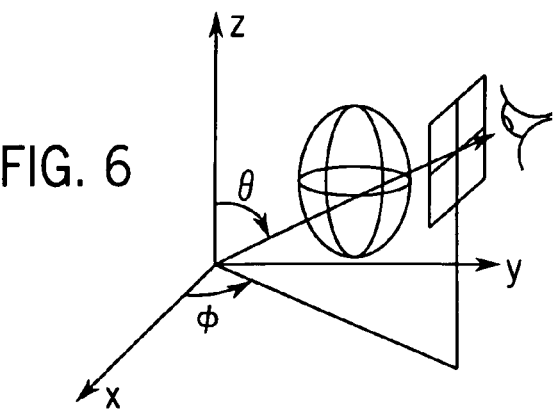
FIG. 6 illustrates the viewing geometry for a 3D translucent reconstruction of an image.
Figure 5A:
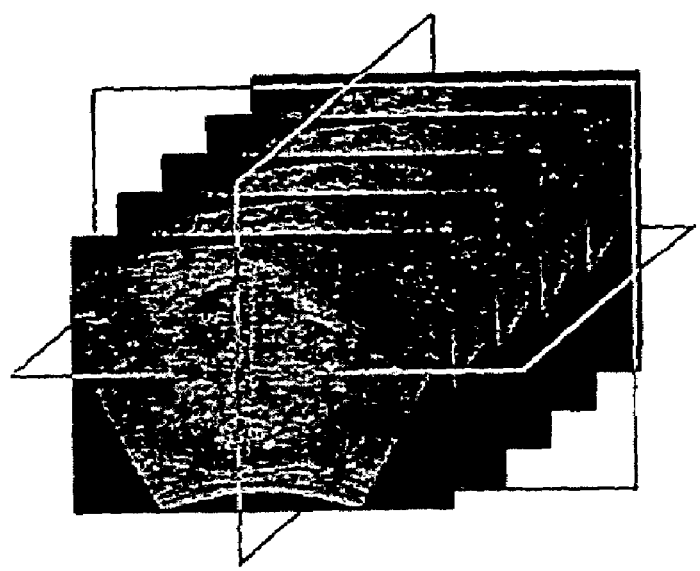
FIG. 5A illustrates reconstruction of standard orthogonal image planes from a 3D image stack and FIG. 5B the reconstruction of oblique image planes from a 3D image stack.
Figure 5B:
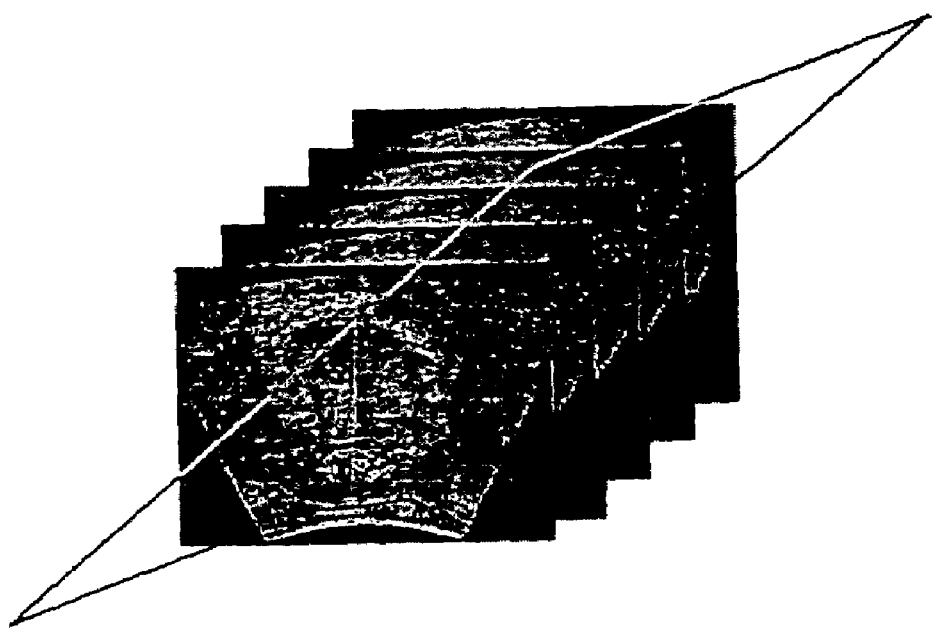
Figure 7A:
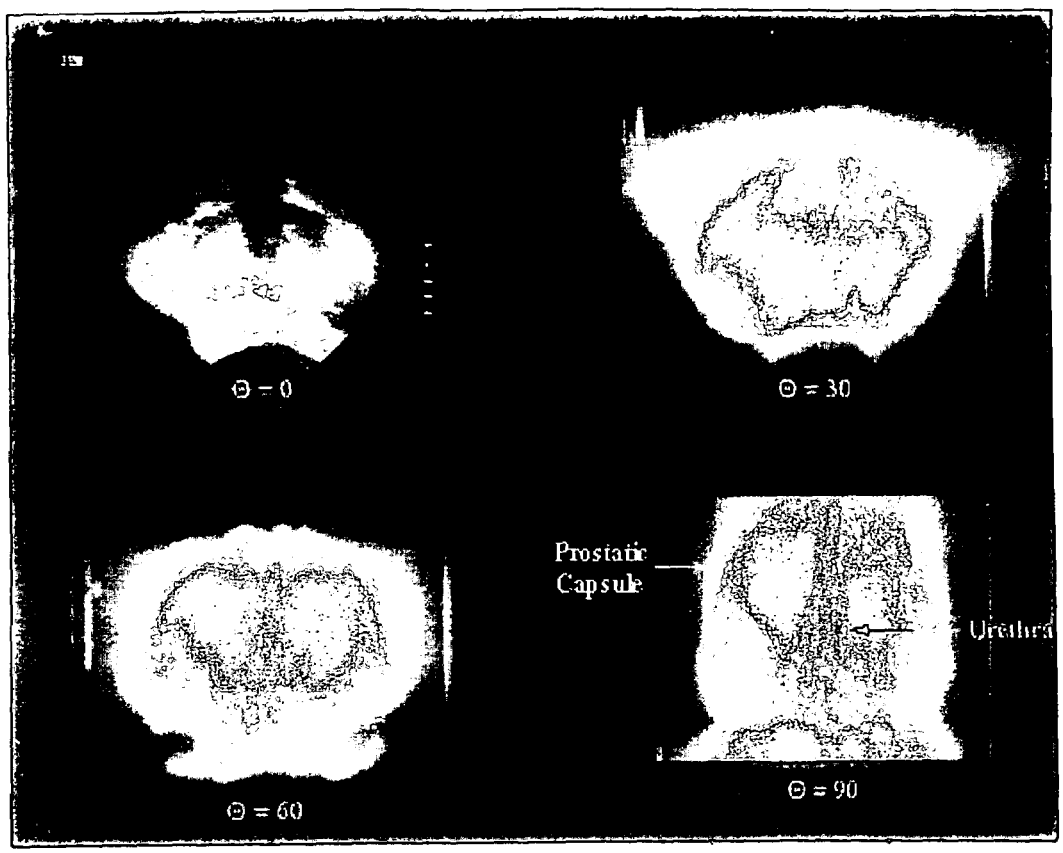
FIG. 7A illustrates translucent images of a human prostate for four different viewing angles and FIG. 7B illustrates translucent images of a phantom organ for six different viewing angles.
Figure 7B:
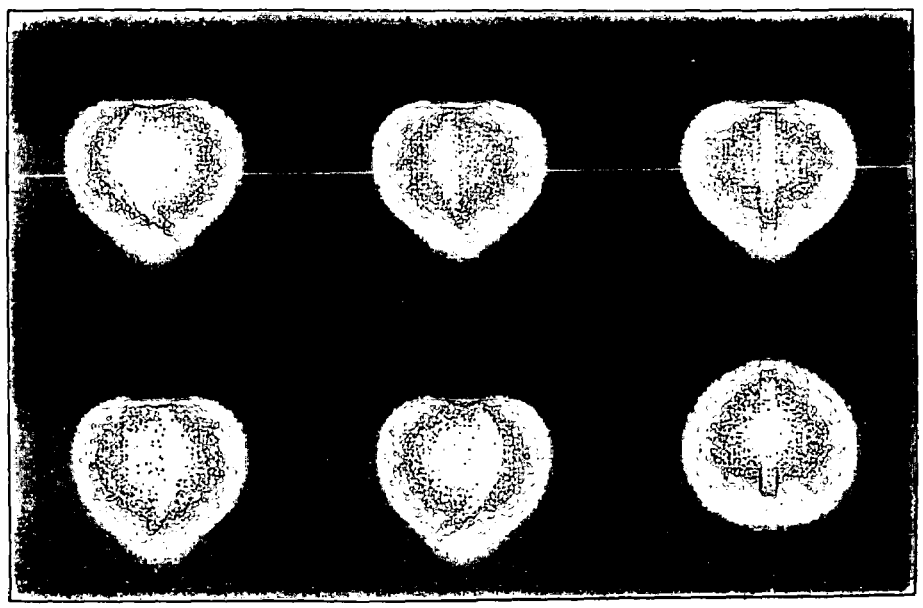

In the preferred embodiment, three of the perspective views are the standard transverse, coronal and sagittal 2D views. These three orthogonal views are taken from a user specified location within the imaging space. For example, the user can request that the three orthogonal views have their common centers at a spatial position of (5.0 cm, 15.0, 25.0 cm) relative to the origin of the template system. One also can select the reference point of either of the three orthogonal views independently, that is the three views do not have to have common center points. As mentioned hereinbefore, FIGS. 5A and 5B show examples of several example 2D views from a 3D ultrasound image volume. FIG. 6 shows a number of possible viewing directions, and FIG. 7 gives further examples of translucent 3D viewing from different angles. The 3D ultrasound image volume was obtained from actual ultrasound images of a human prostate and of a prostate implant phantom.

On each of the views, one can define, draw and edit contours using conventional computer software, such as Microsoft Foundation Class (MFC) view files. Each contour can be given a unique name by the user, and then drawn by the user using the mouse of the computer 16. All attributes of the contours such as name and color can, based on conventional imaging software, be user selectable. The user can also edit the contours by selecting functions, such as adding a point to a contour, deleting a point from a contour or deleting the entire contour. Once the contours are defined, the user has the option to render them in 3D or view in conventional 2D mode on the 3D perspective mode or viewed in the VR mode. Again, all contour 3D attributes such as color, lighting, and shading are user controlled. The contours by default appear on the 2D images, however, the user can control the individual contour's 2D and 3D visibility.

Figure 8:
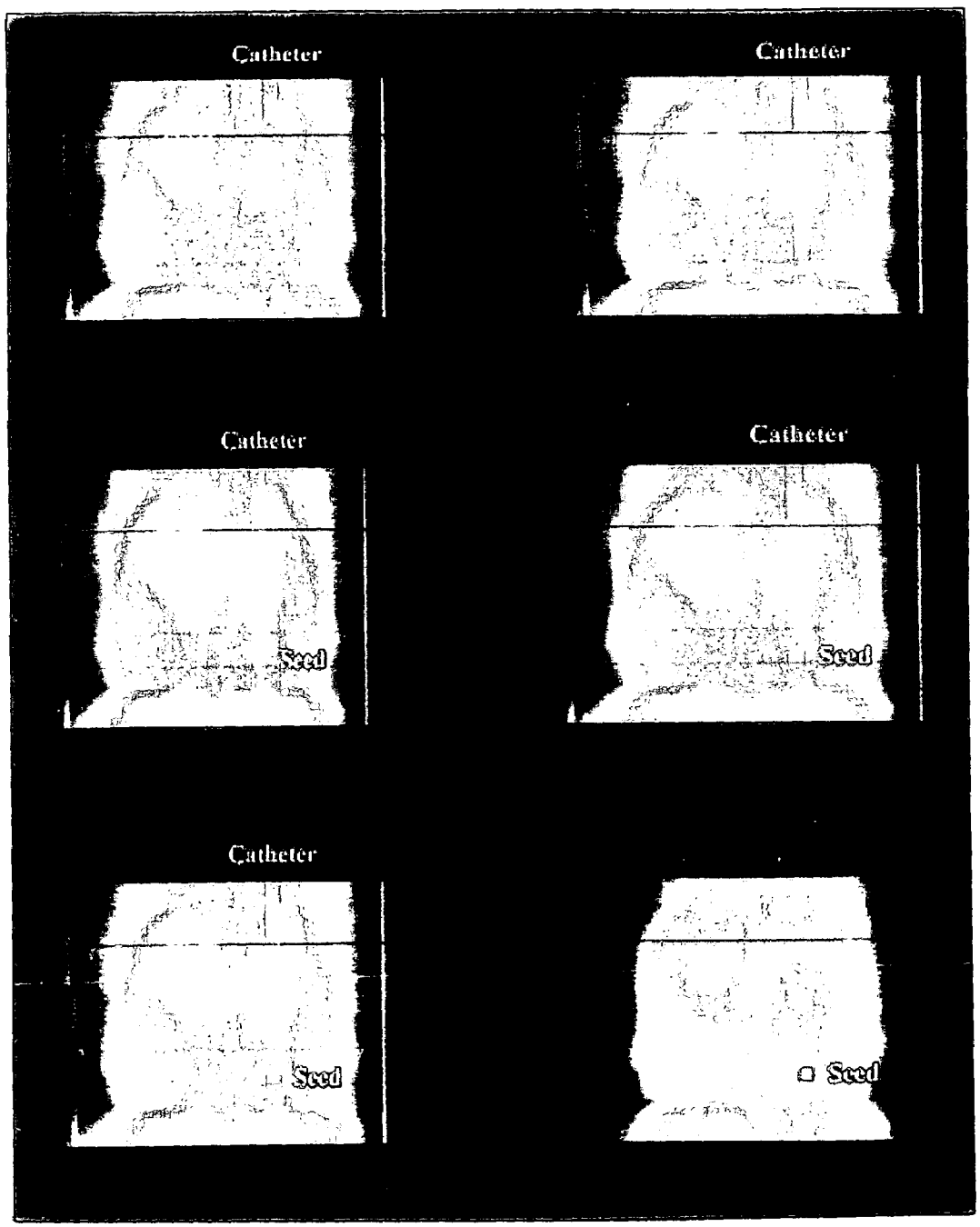
FIG. 8 illustrates a time sequenced image of the prostate organ in FIG. 7A showing approach of a catheter containing a radioactive seed, deposition of the seed and withdrawal of the catheter leaving the seed.

In order to improve the ability to visualize the real time, 3D information, the 3D image raster can be rendered as a real time, transparent, 3D volume. This transparent volume can be viewed and displayed on the monitor of the computer 16 at any arbitrary viewing angle and is calculated using conventional 3D object reconstruction algorithms. Such standard algorithms can render a large imaging volume in fractions of a second, even on present day computing platforms. The transparent nature of the reconstruction thus allows the user to "see" inside any objects which appear in the imaging volume. For example, if the prostate is imaged in the imaging volume, then it will be reconstructed as a transparent volume, in which other anatomical landmarks such as the urethra, tissue abnormalities or calcifications can be seen. In addition, if any other objects such as needles or catheters are inserted into the prostate, and if they are visible in the ultrasound images, they will be seen as they enter the prostate (see FIG. 8 showing introduction of the seed 18 with the catheter/needle 19). Since the volumes are rendered as transparent solids, the needles 19 (and other articles) can thus easily be seen as they move inside the prostate volume as well. Since the ultrasound images are obtained in real time, the 3D perspective reconstruction is also rendered in real time. The preferred algorithm for the perspective 3D reconstruction is the known Bresenham raytrace algorithm.

As described above, in the routine process of brachytherapy planning, the patient undergoes an initial volumetric ultrasound scan using the probe 12. This scan is done before the radiation therapy planning or the actual implant. During the radiation therapy planning, the ideal positions of the radioactive seeds 18 (see FIG. 1) within the prostate are determined. This ideal seed distribution is optimized to deliver a dose distribution within the prostate that will deliver all the radiation dose to the target volume only, while sparing the surrounding healthy tissues such as the rectum and bladder. The optimal positions of the seeds 18 and the optimal position of the needles 19 are recorded for later use in the operating room when the needles 19 are loaded into the patient. The seeds 18 are then loaded into the needles 19, and the physician then attempts to place the needles 19 inside the prostate according to the treatment dose plan positions (again, see example in FIG. 8).

Figure 9:
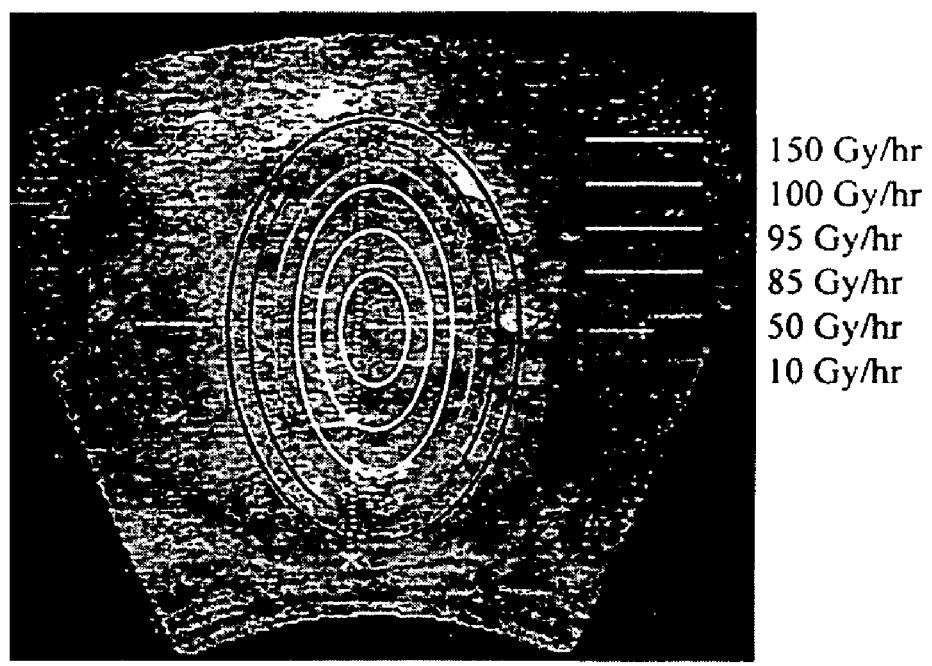
FIG. 9 illustrates isodose distributions of radiation from a single radioactive seed.
Figure 12:
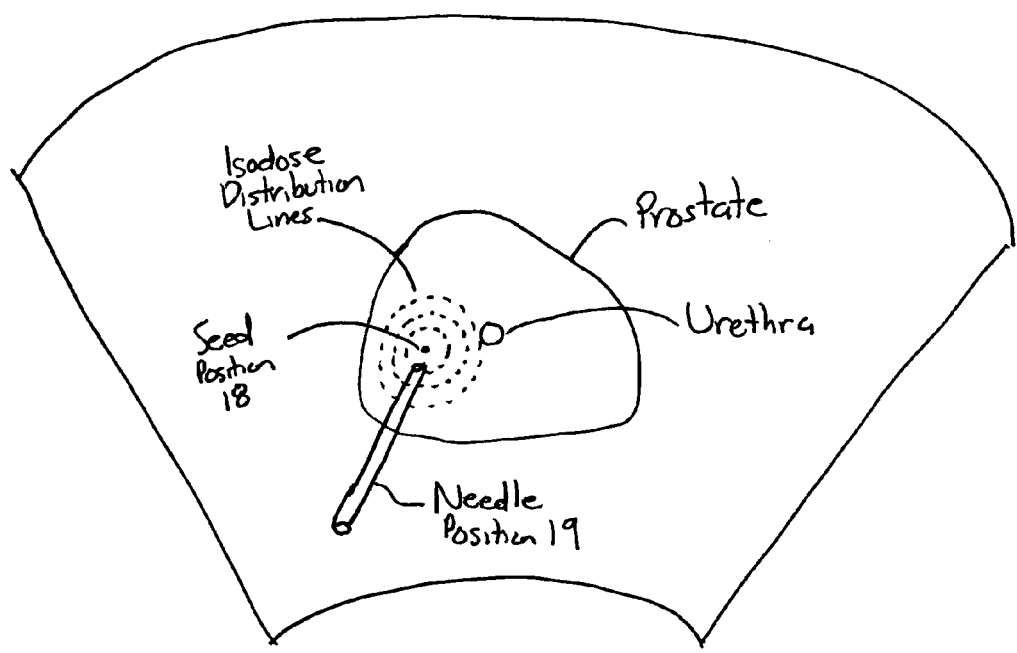
FIG. 12 depicts another illustration of isodose distributions of radiation from a single radioactive seed.

The dose as a function of position for a cylindrical .sup. 125I seed of a given activity can be determined from a lookup table or calculated from a conventional analytic formula. The dose field can be visualized as a set of isodose lines in 2D or isodose surface in 3D (see, for example, FIG. 9 and FIG. 12). The dose computation routine is based upon the TG43 standard adopted by the AAPM (American Association of Physicists in Medicine) entitled "Dosimetry of Interstitial Brachytherapy Sources": Recommendations of the AAPM Radiation Therapy Committee Task Group No. 43 which specifies the dose model and the data used in the dose calculation. This particular implementation runs extremely fast on a conventional 233 MHz PC, computing the dose for a single seed in less than 0.5 seconds. The total 3D dose distribution within the prostate for a 100 seed implant requires only 50 seconds, or less than one minute total computation time. Thus, this can be done "on line" in the operating room.

Figure 13A:
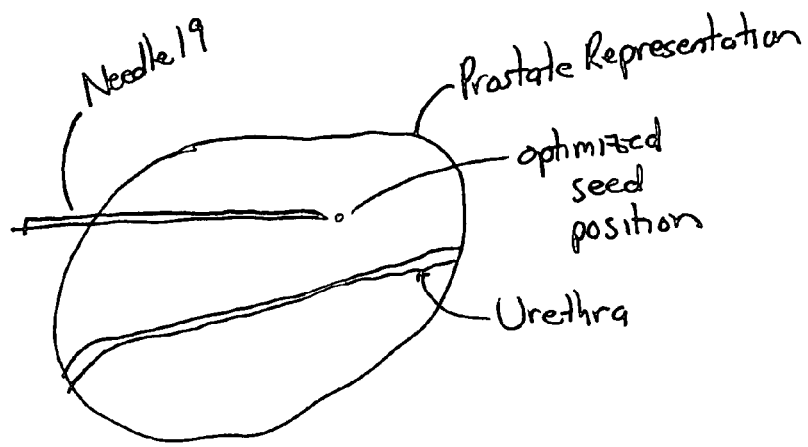
FIGS. 13(a) and 13(b) depict the ability to view optimized seeds and needles in the same volume as the real time ultrasound data.
Figure 13B:
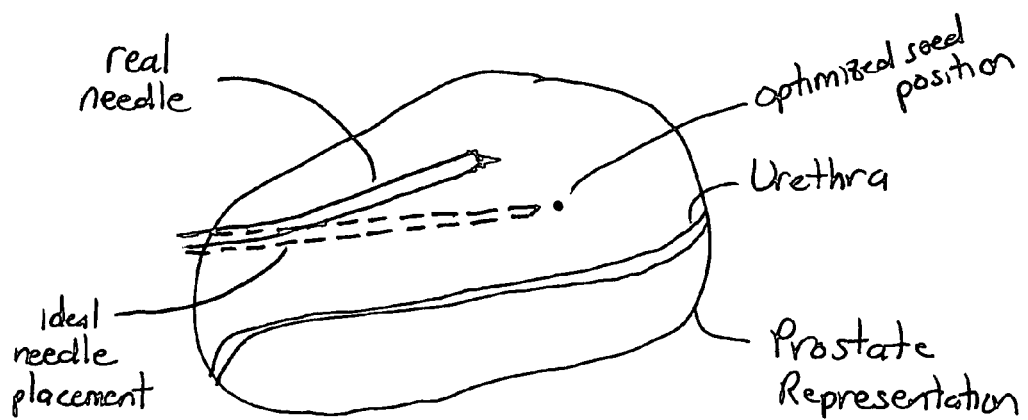

In the 2D, 3D perspective, or the real time VR modes, the user has the ability to view the optimized seeds 18 and the needles 19 in the same volume as the real time ultrasound data (see, for example. FIG. 13(a)). This allows the physician to see exactly where the needles 19 should go and hence make adjustments to position the needles 19 optimally. The pre-planned, optimal positioned needles 19 and the seeds 18 can be rendered again as a transparent solid, the color of which is user selectable. As the real needles 19 are inserted into the prostate, their positions relative to the ideal needle placements based on the dose plan can be monitored in real time (see, for example. FIG. 13(b)). Any deviation of the position of a given needles 19 can be quickly and accurately readjusted so as to follow the path of the ideal needles 19. As the different needles 19 are placed at different positions inside the prostate, the viewing angle can be adjusted to facilitate viewing of the needle or catheter placement. FIGS. 5A and 5B displays perspective 3D views and the three orthogonal reconstructions of the image data along with the pre-planned catheter positions. The pre-planned needles 19 can also be viewed in the VR mode as virtual objects overlaid onto the imaging volume.

Figure 10:
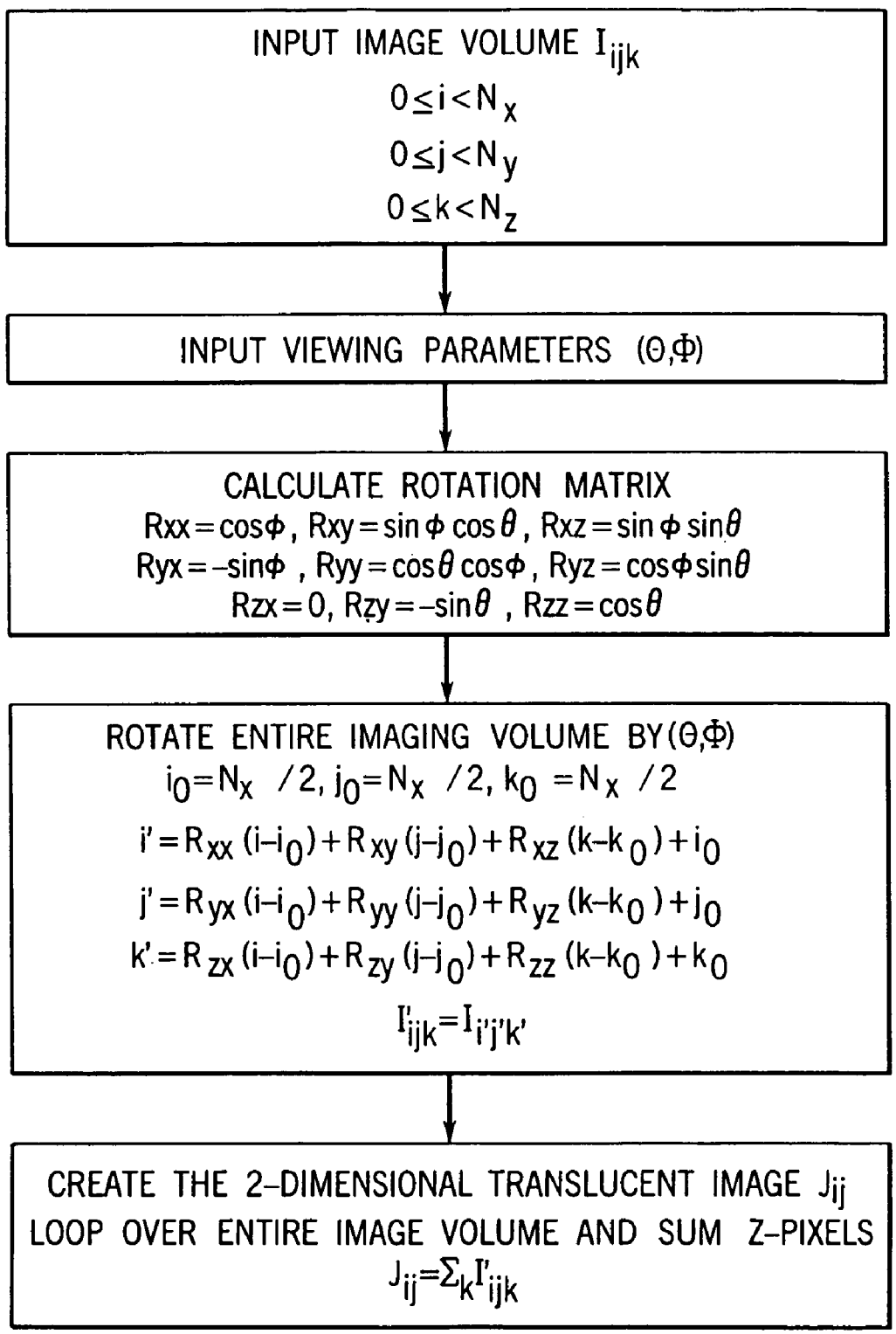
FIG. 10 illustrates a flow chart of software routine for processing imaging data for visualization.

A flowchart description of the translucent volume visualization methodology is shown in FIG. 10. The input image volume is described by the vectors i, j, k of appropriate magnitude for the volume. The viewing angle parameters are the angles θ, Ø described on FIG. 6 and FIG. 10. The rotation matrix, R, is calculated using the formulae given in the flowchart of FIG. 10. The entire imaging volume is calculated by multiplying the rotation matrices in the x, y, z directions by the respective vectors i, j and k describing the incremental portions along the x, y, z directions. Thus, the multiplying vector is $(i-i_o, j-j_o, k-k_o)$ where $i_o, j_o, k_o$ are the starting points along x, y and z axes and the volume is determined by summing the component contributions shown in FIG. 10. The 3D translucent image is then created by computing the translucent 2D image over the entire image volume and summing the z-pixels.

Figure 11:
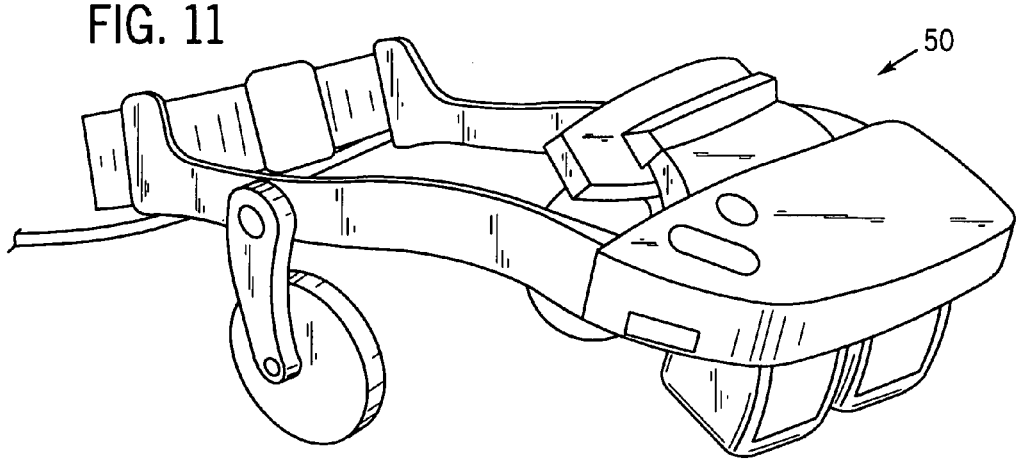
FIG. 11 illustrates a virtual reality head mounted display.

A virtual reality interface system can be composed of a conventional head mounted display (HMD) 50 shown in FIG. 11 and a 6D (x,y,z, roll, pitch, yaw) tracking system. The HMD 50 consists of two color monitors which mount to a head set in the position directly in front of the eyes. The HMD 50 is based on the principal that whatever is displayed on each monitor is directly incident on the retina for each eye, and hence true 3D images can be created by rendering objects as 3D perspective images for each eye. Given the distance between the eyes (the interoccular distance which is approximately 80 mm) and the distance and spherical angles of the distance of the center line between the eyes from the coordinate origin, the 2D images which appear in each of the two monitors can be determined exactly as described above. This results in a true 3D image as perceived by the user. Therefore, as the user moves his or her head or moves around the room, the distance from the origin and the spherical angles also change. This motion of the user or user's head can be obtained from the VR tracking system. Given these spatial parameters, the images which are reconstructed in the two eye monitors can be updated in real time, giving the user the illusion of the object really existing in 3D space. The user literally has the ability to walk around the object, viewing it in 3D space.

Instead of reconstructing computer generated geometric objects as is usually the case in VR, the transparent, 3D reconstruction of the real time imaging data will preferably be reconstructed. Hence as the physician walks around the patient undergoing the implant, the physician will see the 3D ultrasound volume mapped inside the patient's pelvis, spatially correlated to the position of the patient's real prostate (or other organ) and anatomy. The physician can "see" inside the patient to the extent of what is visible in the ultrasound imaging volume. Since the ultrasound probe 12 is locked down to the template, which is then secured to the floor, the exact positions of all voxels in the ultrasound imaging volume are known exactly relative to the template, and hence relative to the room.

As the needles 19 are inserted into the patient, they will appear in the image volume and hence are reconstructed in the VR reconstruction. All of this occurs in real time so that the physician also can see the needles 19 enter the prostate in real time. As mentioned above, if the pre-planned, optimized needles 19 are displayed, the physician can then see the position of the actual needles 19 as they are being inserted relative to the optimal placement. Hence, the physician has the ability to adjust the needles 19 to correspond to their optimal positions. In addition, since the needles 19 are automatically extracted, the computer software has the ability to calculate and render the 3D dose distribution in real time as the needles 19 are being inserted.

As an example, a currently available, a fast and inexpensive HMD is made by Virtual-IO Corporation (Mountain View, Calif.). The HMD is full color with two 0.70 LCD displays with a resolution of 180,000 pixels per LCD panel. The video input is NTSC with field sequential format. The LCD panels are semitransparent, allowing the real outside world to be included in the virtual reconstruction. The field of view is 30° for each eye. A six degree of freedom (6 DOF) tracking system can also be attached to the HMD. The 6 DOF tracking system allows for the determination of the spatial position of the user's head and the yaw, pitch, and roll of the head. The conventional head set weighs only 8 ounces and comes with stereo sound. Stereo sound is an extremely valuable technology in the operating room. With this capability, the physician has the ability to monitor the patient's heart rate and respiration rate while performing the implant. Hence any fluctuation in the patient's vital signs can be instantly accessed and acted thereon if necessary.

The radioactive seeds 18 are made of high density material such as stainless steel, and hence have a very bright response in the ultrasound images. Therefore, automatic seed detection in the ultrasound images can readily be accomplished, for example, by a simple thresholding algorithm along with the requirement that the resultant objects which are removed by threshold have a certain maximum size determined by the actual size of the seeds.

Near-real-time visualization will provide immediate feedback to the physician during the implant process itself. There is a clear need for the visualization being available during the implant process. The nearly real time visualization is of great importance to the effective use of a translucent overlay of the ideal seed pre-plan (from the therapy planning process) in the three-dimensional volume. The physician can "see" in nearly real time the relationship of the needles and seeds being implanted to the ideal pre-plan locations and quickly accommodate redirection required prior to leaving the radiation seeds. Further, the need for this in three-dimensional representation is very important to overcome the greatest fundamental limitation in brachytherapy, which is knowing at the same time both the lateral placement and longitudinal placement of needles and seeds relative to the target volume and pre-plan. This is a 3D problem which has up until now been addressed in 2D in a stepwise fashion without the ability to "see" the exact location of where you are in the target. This real time 3D visualization also would speed the implant process in the case of brachytherapy as well as make it more accurate. It would also speed other minimally invasive surgical procedures and localized tissue ablation procedures (for example, cryosurgery or localized selected ablation of diseased liver tissue or local removal of breast tissue). These procedures could be accomplished with real time visualization inside the tissue being treated with greater accuracy in shorter time. This aspect would reduce operating room time and costs to the patient and health care system.

While preferred embodiments of the inventions have been shown and described, it will be clear to those skilled in the art that various changes and modifications can be made without departing from the invention in its broader aspects as set forth in the claims provided hereinafter.

What is claimed is:

1. A computer-readable medium for facilitating performance of medical therapy treatment on a patient, the computer-readable medium comprising:
   one or more instructions executable by a processor for processing real-time image data to generate in substantially real time an image of a treatment region of a patient's body along with an image of a therapeutic device inserted inside the patient's body relative to the treatment region, the therapeutic device including a radiation source;
   one or more instructions executable by a processor for retrieving a planned dose spatial distribution for the patient's body, the planned dose spatial distribution corresponding to a planned position for the radiation source; and
   one or more instructions executable by a processor for displaying, in substantially real time and in spatial registration with each other, the real time treatment region image, the therapeutic device, the radiation source and the planned dose spatial distribution, wherein at least one of the real time treatment region image and the planned dose spatial distribution is displayed as a translucent image.

2. The computer-readable medium of claim 1, further comprising:
   one or more instructions executable by a processor for retrieving a plan image of the treatment region; and
   one or more instructions executable by a processor for displaying the plan image concurrently and in spatial registration with the real time treatment region image, the therapeutic device, the radiation source and the planned dose spatial distribution.

3. The computer-readable medium of claim 2, further comprising:
   one or more instructions executable by a processor for determining an actual position of the radiation source that has been inserted within the treatment region;
   one or more instructions executable by a processor for calculating an actual dose spatial distribution for the patient's body, the actual dose spatial distribution corresponding to the determined actual position of the radiation source within the treatment region; and
   one or more instructions executable by a processor for displaying the actual dose spatial distribution concurrently and in spatial registration with the plan image, the real time treatment region image, the therapeutic device, the radiation source and the planned dose spatial distribution.

4. The computer-readable medium of claim 3, further comprising:
one or more instructions executable by a processor for retrieving a planned position for the therapeutic device; and
one or more instructions executable by a processor for displaying the planned position for the therapeutic device concurrently and in spatial registration with the plan image, the real time treatment region image, the therapeutic device, the radiation source, the planned dose spatial distribution and the actual dose spatial distribution, wherein the planned position for the therapeutic device is displayed as a translucent image.

5. The computer-readable medium of claim 1, further comprising:
one or more instructions executable by a processor for displaying, in substantially real time and in spatial registration with each other, the real time treatment region image, the therapeutic device, the radiation source and the planned dose spatial distribution, wherein both the real time treatment region image and the planned dose spatial distribution is displayed as a translucent image.

6. The computer-readable medium of claim 1, further comprising:
one or more instructions executable by a processor for three-dimensionally displaying, in substantially real time and in spatial registration with each other, the real time treatment region image, the therapeutic device, the radiation source and the planned dose spatial distribution, wherein at least one of the real time treatment region image and the planned dose spatial distribution is displayed as a translucent image.

7. A method of performing medical imaging, comprising the steps of:
obtaining real time image data relating to a treatment region of a patient, a radiation source and a therapeutic device, wherein the treatment region includes at least an organ of the patient;
obtaining plan image data of the treatment region, the plan image data comprising an image of the treatment region and the patient organ, a planned position for a radiation source, and a planned dose spatial distribution for the planned radiation source position;
generating in substantially real time a three dimensional image of the treatment region and the radiation source based on the real time image data relating to the treatment region and the radiation source;
generating a three dimensional image of the therapeutic device based on the real time image data relating to the therapeutic device; and
displaying simultaneously the three dimensional real time image of the treatment region, the radiation source and the image of the therapeutic device, wherein the three dimensional real time images of the treatment region, the radiation source and the therapeutic device have a coordinated spatial reference frame; and
wherein the three dimensional real time image of the treatment region is displayed as a translucent three-dimensional image; and
wherein the displaying step further comprises simultaneously displaying the plan image data in spatial registration with the three dimensional real time image of the treatment region and the radiation source and the image of the therapeutic device.

8. A method for simultaneously displaying data corresponding to a treatment plan and medical images, the method comprising the steps of:
providing an image of a pre-treatment dose plan, the pre-treatment dose plan comprising a planned position for a radiation source within a treatment region of a patient's body and a planned dose distribution corresponding to the planned radiation source position;
determining a position for a therapeutic device including a radiation source that has been inserted into the treatment region;
registering the determined position with the planned radiation source position;
determining a dose distribution from the inserted radiation source;
registering the determined dose distribution with the planned dose distribution;
obtaining real time image data of the therapeutic device relative to the treatment region;
registering in substantially real time the spatial position of the inserted radiation source relative to the treatment region based on the determined position of the therapeutic device; and
concurrently displaying in substantially real time the determined therapeutic device position, the planned radiation source position, the planned dose distribution, and the determined dose distribution, all in spatial registration with each other.

9. A system for assisting in a performance of medical therapy treatment on a patient, the system comprising:
an imaging component configured to generate in substantially real time an image, the real time image comprising a treatment region of a patient's body, a therapeutic device that has been inserted into the treatment region, and a radiation source inserted into the treatment region via the therapeutic device;
a processing component in communication with the imaging component, the processing component being configured to (1) determine from the real time image a position for the inserted radiation source, (2) calculate a radiation dose distribution in the patient's body based at least in part upon the determined position for the inserted radiation source, and (3) spatially register the calculated radiation dose distribution with a planned radiation dose distribution for the patient; and
a displaying component in communication with the processing component, the displaying component being configured to simultaneously display the real time image, the calculated radiation dose distribution and the planned radiation dose distribution, all in spatial registration with each other.

10. The system of claim 9, wherein the processing component is further configured to spatially register a plan image of the treatment region and a planned position for a radiation source with the real time image and the calculated radiation dose distribution, and wherein the displaying component is further configured to simultaneously display the real time image, the plan image, the inserted radiation source, the planned radiation source position, the calculated radiation dose distribution and the planned radiation dose distribution, all in spatial registration with each other, and wherein at least one of the real time image, the planned radiation source position, and the planned radiation dose distribution is displayed as a translucent image.

11. The system of claim 10, wherein at least two of the real time image, the planned radiation source position, and the planned radiation dose distribution are displayed as translucent images, and wherein each translucent image exhibits a user-controlled degree of translucency.

12. The system of claim 10, wherein the medical therapy treatment comprises prostate brachytherapy and wherein the displaying component is further configured to simultaneously display the real time image, the plan image, the inserted radiation source, the planned radiation source position, the calculated radiation dose distribution and the planned radiation dose distribution as three-dimensional images.

13. A computer-readable medium for facilitating a performance of medical therapy treatment on a patient, the computer-readable medium comprising:
  one or more instructions executable by a processor for processing real time image data to generate in substantially real time an image of a treatment region of a patient's body, the treatment region comprising a region of interest, portions of the patient's body near the region of interest, a therapeutic device that has been inserted into the treatment region, and a radiation source that has been inserted into the treatment region via the inserted therapeutic device;
  one or more instructions executable by a processor for calculating an actual dose spatial distribution for the patient's body based at least in part upon the inserted radiation source;
  one or more instructions executable by a processor for separately contouring from the real time image at least a portion thereof, thereby generating at least one contoured image;
  one or more instructions executable by a processor for simultaneously displaying the real time image, the at least one contoured image, a plan image of the treatment region, the actual dose spatial distribution, a planned dose distribution, a planned position for the therapeutic device, and a planned position for a radiation source, all in spatial registration with one another; and
  one or more instructions executable by a processor for rendering and displaying at least one selected from the group consisting of the real time image, the at least one contoured image, the planned dose distribution, the planned position for the therapeutic device, and the planned radiation source position as a translucent image.

14. The computer-readable medium of claim 13, wherein the translucent rendering and displaying instructions comprise one or more instructions executable by a processor for rendering and displaying at least two selected from the group consisting of the real time image, the at least one contoured image, the planned dose distribution, the planned position for the therapeutic device, and the planned radiation source position as translucent images.

15. The computer-readable medium of claim 14, wherein the translucent rendering and displaying instructions comprise one or more instructions executable by a processor for rendering and displaying the at least two translucent images with different translucent appearances.

16. The computer-readable medium of claim 13, wherein the translucent rendering and displaying instructions comprise one or more instructions executable by a processor for rendering and displaying at least the real time image and the planned dose distribution as translucent images.

17. The computer-readable medium of claim 13, wherein the translucent rendering and displaying instructions comprise one or more instructions executable by a processor for rendering and displaying at least the real time image and the planned position for the therapeutic device as translucent images.

18. The computer-readable medium of claim 13, wherein the real time image data comprises ultrasound image data, and wherein real time image, the at least one contoured image, a plan image of the treatment region, the actual dose spatial distribution, the planned dose distribution, the planned position for the therapeutic device, and the planned position for a radiation source are displayed as three-dimensional images.

19. A method for performing medical therapy treatment on a patient, comprising the steps of:
  inserting a therapeutic device including a radiation source into a treatment region of a patient's body;
  obtaining image data of the therapeutic device relative to the treatment regions
  registering in substantially real time the spatial position of the radiation source relative to the treatment region based on the position of the therapeutic device;
  calculating in substantially real time a dose spatial distribution for the radiation source relative to the treatment region;
  displaying in substantially real time an image of the treatment region, the therapeutic device, the radiation source and the dose spatial distribution; and
  leaving the radiation source in the patient as part of a long term treatment procedure.

20. A system for performing medical therapy treatment on a patient, comprising:
  an imaging component for generating in substantially real time an image of a treatment region of a patient's body along with an image of a therapeutic device relative to the treatment region, the therapeutic device including a radiation source and having been inserted into the patient's body;
  a calculating component for calculating dose distribution in the patient's body of the radiation source after the radiation source has been inserted into the patient's body via the therapeutic device; and
  a displaying component for simultaneously displaying an image of the treatment region, the therapeutic device, the radiation source, a planned dose distribution for a planned position of a radiation source, and the calculated dose distribution, all in spatial registration with one another; and
  wherein the component for generating includes a component for obtaining two dimensional image slices of the treatment region to form a three dimensional image of the treatment region of the patient's body; and
  wherein the two dimensional images slices are obtained using an ultrasound probe mounted on a movable holder for positioning the ultrasound probe; and
  wherein the movable holder includes a stepper device which includes a digital encoder to determine the spatial position of the probe.

21. The system of claim 20, wherein the image of the treatment region, the therapeutic device, the radiation source, and the planned dose distribution for the planned position of the radiation source are displayed in substantially real-time, and wherein the holder contains a template having openings for passage of the therapeutic device through said template into the treatment region.

22. The system of claim 21, wherein the template is comprised of a disposable material for a single use treatment.

23. An imaging system for use in connection with a performance of medical treatment on a patient's body, the system comprising:
  an imaging device for obtaining image data in substantially real time, the image data comprising a treatment region of the patient's body, at least one radiation source that has been inserted inside the treatment region, and at least one therapeutic device that has been inserted inside the treatment region, the treatment region comprising a region of interest and portions of the treatment region near the region of interest;
  a processor in communication with the imaging device, the processor configured to (1) retrieve a treatment plan for the patient's medical treatment, the treatment plan comprising plan image data for the region of interest, at least one planned position for placement of a radiation source, and a planned spatial radiation dose distribution for each planned position, (2) generate a plan image from the treatment plan image data, (3) generate in substantially real time an image of the treatment region, the at least one inserted radiation source, and at least one inserted therapeutic device, (4) calculate a spatial radiation dose distribution for the at least one inserted radiation source, and (5) spatially register the plan image, the at least one planned radiation source placement position, and the planned spatial radiation dose distribution with the calculated spatial radiation dose distribution and the image of the treatment region, the at least one inserted radiation source, and the at least one inserted therapeutic device; and
  a display device in communication with the processor, the display device being configured to simultaneously display, in spatial registration with each other, the plan image, an indicator for the at least one planned radiation source placement position, the planned spatial radiation dose distribution, the calculated spatial radiation dose distribution, and the image of the treatment region, the at least one inserted radiation source, the at least one inserted therapeutic device.

24. The system of claim 23 wherein the image of the treatment region, the at least one inserted radiation source, and the at least one inserted therapeutic device comprises a three-dimensional (3D) image.

25. The system of claim 24 wherein the planned and calculated spatial radiation dose distributions comprise 3D spatial radiation dose distributions.

26. The system of claim 25 wherein the plan image comprises a 3D image.

27. The system of claim 26 wherein the plan image further comprises an image of the region of interest and the treatment region.

28. The system of claim 26 wherein the imaging device comprises an ultrasound probe.

29. The system of claim 28 wherein the region of interest is a patient's prostate.

30. The system of claim 29 wherein the therapeutic device comprises a needle and catheter.

31. The system of claim 26 wherein the display device is further configured to simultaneously display, in spatial registration with each other and in substantially real time, the plan image, an indicator for the at least one planned radiation source placement position, the planned spatial radiation dose distribution, the calculated spatial radiation dose distribution, and the image of the treatment region, the at least one inserted radiation source, the at least one inserted therapeutic device.

32. The system of claim 23 wherein the processor is further configured to generate a translucent image of the treatment region, the at least one inserted radiation source, and the at least one inserted therapeutic device and a translucent indicator for the planned radiation source placement position, and wherein the display device is further configured to simultaneously display, in spatial registration with each other, the plan image, the translucent indicator for the at least one planned radiation source placement position, the planned spatial radiation dose distribution, the calculated spatial radiation dose distribution, and the translucent image of the treatment region, the at least one inserted radiation source, the at least one inserted therapeutic device.

33. The system of claim 32 wherein the translucency of the translucent indicator and the translucent image of the treatment region, the at least one inserted radiation source, the at least one inserted therapeutic device are user-controlled.

34. The system of claim 32 wherein the processor is further configured to generate a translucent planned spatial radiation dose distribution, and wherein the display device is further configured to simultaneously display, in spatial registration with each other, the plan image, the translucent indicator for the at least one planned radiation source placement position, the translucent planned spatial radiation dose distribution, the calculated spatial radiation dose distribution, and the translucent image of the treatment region, the at least one inserted radiation source, the at least one inserted therapeutic device.

35. The system of claim 34 wherein the translucency of the translucent indicator, the translucent planned spatial radiation dose distribution, and the translucent image of the treatment region, the at least one inserted radiation source, the at least one inserted therapeutic device are user-controlled.

36. The system of claim 34 wherein the processor is further configured to generate a translucent plan image, and wherein the display device is further configured to simultaneously display, in spatial registration with each other, the translucent plan image, the translucent indicator for the at least one planned radiation source placement position, the translucent planned spatial radiation dose distribution, the calculated spatial radiation dose distribution, and the translucent image of the treatment region, the at least one inserted radiation source, the at least one inserted therapeutic device.

37. The system of claim 36 wherein the translucency of the translucent plan image, the translucent indicator, the translucent planned spatial radiation dose distribution, and the translucent image of the treatment region, the at least one inserted radiation source, the at least one inserted therapeutic device are user-controlled.

38. The system of claim 23 wherein the processor is further configured to generate a translucent image of the treatment region, the at least one inserted radiation source, and the at least one inserted therapeutic device and a translucent planned spatial radiation dose distribution, and wherein the display device is further configured to simultaneously display, in spatial registration with each other, the plan image, the indicator for the at least one planned radiation source placement position, the translucent planned spatial radiation dose distribution, the calculated spatial radiation dose distribution, and the translucent image of the treatment region, the at least one inserted radiation source, the at least one inserted therapeutic device.

39. A system for generating and displaying images for use in connection with a radiation treatment performed upon a patient, wherein the radiation treatment is based at least in part upon a treatment plan, the treatment plan comprising a planned position for at least one radiation source within the patient's body and a planned radiation dose distribution for radiation source based on at least in part upon the planned position, the system comprising:

an imaging device configured to obtain image data of a patient's treatment region in substantially real-time, the treatment region comprising a region of interest, portions of a patient's body near the region of interest, and at least one radiation source that has been inserted in the patient's body as part of the radiation treatment; and a computer in communication with the imaging device, the computer being configured to (1) access data describing the treatment plan and (2) process the image data from the imaging device and the treatment plan data to calculate and display an actual radiation dose distribution for the at least one inserted radiation source, wherein the actual radiation dose distribution is displayed concurrently and in spatial registration with the planned radiation dose distribution from the treatment plan.

40. The system of claim 39 wherein the computer is further configured to display the planned radiation dose distribution translucently.

41. The system of claim 40 wherein the treatment plan further comprises a planned position for a delivery device, the delivery device for delivering the at least one radiation source to the planned position, wherein the treatment region further comprises the delivery device that has been inserted into the patient's body to deliver the radiation source, and wherein the computer is further configured to process the image data from the imaging device and the treatment plan data to also display the actual delivery device concurrently with an in spatial registration with the planned position for the delivery device.

42. The system of claim 41 wherein the computer is further configured to display the planned position for the delivery device translucently.

43. The system of claim 42 wherein the computer is further configured to translucently display the planned radiation dose distribution and the planned position for the delivery device in accordance with a user-specified degree of translucency.

44. The system of claim 40 wherein the radiation treatment comprises prostate brachytherapy.

45. The system of claim 39 wherein the actual radiation dose distribution and the planned radiation dose distribution from the treatment plan are concurrently displayed as three-dimensional radiation dose distributions.

* * * * *